(12) United States Patent
Eguchi

(10) Patent No.: US 11,241,205 B2
(45) Date of Patent: Feb. 8, 2022

(54) RADIOGRAPHY APPARATUS

(71) Applicant: FUJIFILM Corporation, Tokyo (JP)

(72) Inventor: Koichi Eguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/032,842

(22) Filed: Sep. 25, 2020

(65) Prior Publication Data

US 2021/0093267 A1 Apr. 1, 2021

(30) Foreign Application Priority Data

Sep. 30, 2019 (JP) .............................. JP2019-180017

(51) Int. Cl.
*A61B 6/00* (2006.01)

(52) U.S. Cl.
CPC .......... *A61B 6/4441* (2013.01); *A61B 6/4405* (2013.01); *A61B 6/54* (2013.01)

(58) Field of Classification Search
CPC ....... A61B 5/4441; A61B 6/54; A61B 6/4405; A61B 6/548; A61B 6/4476; A61B 6/547; A61B 6/4458; A61B 6/4283
See application file for complete search history.

(56) References Cited

U.S. PATENT DOCUMENTS 6,609,826 B1 * 8/2003 Fujii ...................... A61B 6/12
378/197

FOREIGN PATENT DOCUMENTS

JP 6-70918 A 3/1994

* cited by examiner

*Primary Examiner* — Don K Wong
(74) *Attorney, Agent, or Firm* — Birch, Stewart, Kolasch & Birch, LLP

(57) ABSTRACT

A radiography apparatus includes: an irradiation unit that emits radiation; an arm that can hold the irradiation unit and an image receiving unit in a facing posture; a connection portion or a main body that supports the arm; a rotation mechanism that rotates the arm with respect to the connection portion or the main body; and an operation handle that is provided independently of the arm and is manually operated to input an operation force for displacing the arm to the rotation mechanism.

20 Claims, 18 Drawing Sheets

RADIOGRAPHY APPARATUS

CROSS-REFERENCE TO RELATED APPLICATIONS

The present application claims priority under 35 U.S.C. § 119 to Japanese Patent Application No., 2019-180017 filed on Sep. 30, 2019. The above application is hereby expressly incorporated by reference, in its entirety, into the present application.

BACKGROUND

1. Technical Field

The present disclosure relates to a radiography apparatus.

2. Description of the Related Art

A radiography apparatus (X-ray apparatus) has been known which includes an arm having two ends. An irradiation unit (X-ray tube) that emits radiation is provided at one end of the arm. An image receiving unit (image receiving device) that receives the radiation emitted from the irradiation unit is provided at the other end of the arm. This arm is supported so as to be rotatable with respect to a main body of the radiography apparatus. The arm is rotated such that the irradiation unit and the image receiving unit can be positioned in any posture around a subject while maintaining a facing posture.

In addition, in a radiography apparatus disclosed in JP1994-070918A (JP-H06-070918A), an arm can be manually rotated. The arm is directly operated to be rotated.

SUMMARY

As the radiography apparatus disclosed in JP1994-070918A (JP-H06-070918A), in many cases, a radiography apparatus which has an arm holding an irradiation unit and an image receiving unit is used during surgery. During surgery, a surgeon may operate the arm or an assistant who assists the surgeon may operate the arm. However, for example, blood may adhere to a portion that is gripped by the surgeon to operate the arm. It is not hygienically preferable that the assistant grips the portion.

An object of the technology according to the present disclosure is to provide a radiography apparatus in which an arm can be manually operated without being directly operated.

According to a first aspect of the present disclosure, there is provided a radiography apparatus comprising: an irradiation unit that emits radiation; an arm that is capable of holding the irradiation unit and an image receiving unit that receives the radiation, which has been emitted from the irradiation unit and transmitted through a subject, in a facing posture; a support portion that supports the arm; a displacement mechanism that displaces the arm with respect to the support portion; and an operation handle that is provided independently of the arm and is manually operated to input an operation force for displacing the arm with respect to the displacement mechanism.

According to the above-mentioned configuration, the operation handle makes it possible to manually operate the arm, without directly operating the arm. Further, since the arm is displaced through the displacement mechanism, the amount of displacement of the arm can be adjusted more easily than that in a case in which the arm is directly operated.

That is, the gear ratio of the displacement mechanism can be set to adjust the relationship between the amount of operation of the operation handle and the amount of displacement of the arm. Therefore, the setting of reducing the amount of displacement of the arm with respect to the amount of displacement of the operation handle is relatively simple. The operation handle makes it easy to finely adjust the amount of displacement of the arm.

In many cases, the arm that holds the irradiation unit and the image receiving unit is used during surgery. Since the operation handle is provided independently of the arm, it is possible to separate an operation part operated by the operator from an operation part operated by the assistant. Therefore, the following method can also be used: the assistant rotates the arm while avoiding the operation part contaminated by contact with the operator.

According to a second aspect of the present disclosure, in the radiography apparatus according to the first aspect, the arm may be displaced by only a manual operation.

According to the above-mentioned configuration, the arm is not rotated by an electromotive force, but can be rotated by only a manual operation. Therefore, it is possible to reduce the size and weight of the entire radiography apparatus. Further, in the case of an electric operation, it is easy to finely adjust the amount of displacement of the arm. However, in the manual operation, in a case in which the arm is directly operated, it is difficult to finely adjust the amount of displacement. Therefore, the technology of the present disclosure is particularly effective for an apparatus with a small size and weight in which the arm is displaced by only a manual operation.

According to a third aspect of the present disclosure, in the radiography apparatus according to the first aspect or the second aspect, the displacement mechanism may be a rotation mechanism that rotates the arm.

According to the above configuration, the operation handle inputs an operation force to the rotation mechanism that rotates the arm. Operations performed during surgery include a slide operation of sliding the arm in the horizontal direction and a rotation operation of rotating the arm. It is considered that the rotation operation is more frequently performed than the slide operation. Therefore, the technology of the present disclosure is particularly effective in a case in which the operation handle is combined with the rotation mechanism.

According to a fourth aspect of the present disclosure, in the radiography apparatus according to the third aspect, the rotation mechanism may have a rotation shaft that is rotated with the rotation of the arm. The operation handle may have a handle shaft that is rotated with rotation of the operation handle. The operation force may be input to the rotation mechanism by a connection between the rotation shaft and the handle shaft.

According to the above-mentioned configuration, the rotation shaft of the rotation mechanism and the handle shaft of the operation handle are connected to form a relatively simple configuration.

According to a fifth aspect of the present disclosure, the radiography apparatus according to the fourth aspect may further comprise a switching mechanism that switches between a valid state in which the input of the operation force from the operation handle to the rotation mechanism is validated and an invalid state in which the input is invalidated.

According to the above-mentioned configuration, the operative association between the rotation mechanism and the operation handle can be switched by the switching mechanism. Therefore, in a case in which the arm is directly rotated, it is possible to prevent the operation handle from being rotated with the rotation of the arm.

According to a sixth aspect of the present disclosure, in the radiography apparatus according to the fifth aspect, the switching mechanism may slide the operation handle in an axial direction to switch between the valid state and the invalid state.

According to the above-mentioned configuration, since the operation handle is slid in the axial direction to switch between the valid state and the invalid state. Therefore, it is possible to switch the operative association between the rotation mechanism and the operation handle with a simple operation.

According to a seventh aspect of the present disclosure, in the radiography apparatus according to the fifth aspect or the sixth aspect, the switching mechanism may bias the operation handle in a direction in which the operation handle is switched to the invalid state.

According to the above-mentioned configuration, the operation handle is manually slid in the axial direction against the biasing force to switch the operation handle to the valid state. The operation handle can be switched to the invalid state only by releasing the hand from the operation handle.

According to an eighth aspect of the present disclosure, in the radiography apparatus according to any one of the fourth to seventh aspects, the arm may have an arc shape in a side view. The rotation mechanism may include a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft. The arm may be moved with respect to the track portion to be orbitally rotated about a center of the arc shape as a rotation center.

According to the above-mentioned configuration, since the arm can be orbitally rotated along the arc shape, the irradiation unit and the image receiving unit can be rotated about the body axis of the subject.

According to a ninth aspect of the present disclosure, in the radiography apparatus according to any one of the fourth to eighth aspects, the rotation mechanism may include a second rotation mechanism comprising a second rotation shaft as the rotation shaft that has one end fixed to the arm and a bearing that is provided in the support portion. The arm may be rotated about the second rotation shaft with respect to the bearing to reverse positions of the irradiation unit and the image receiving unit with respect to the subject.

According to the above-mentioned configuration, since the arm is rotatable about the rotation shaft, it is possible to switch between an overtube posture in which the irradiation unit is disposed above the image receiving unit and an undertube posture in which the irradiation unit is disposed below the image receiving unit.

According to the technology of the present disclosure, it is possible to manually operate the arm without directly operating the arm.

BRIEF DESCRIPTION OF THE DRAWINGS

Exemplary embodiments according to the technique of the present disclosure will be described in detail based on the following figures, wherein.

DETAILED DESCRIPTION

Figure 1:
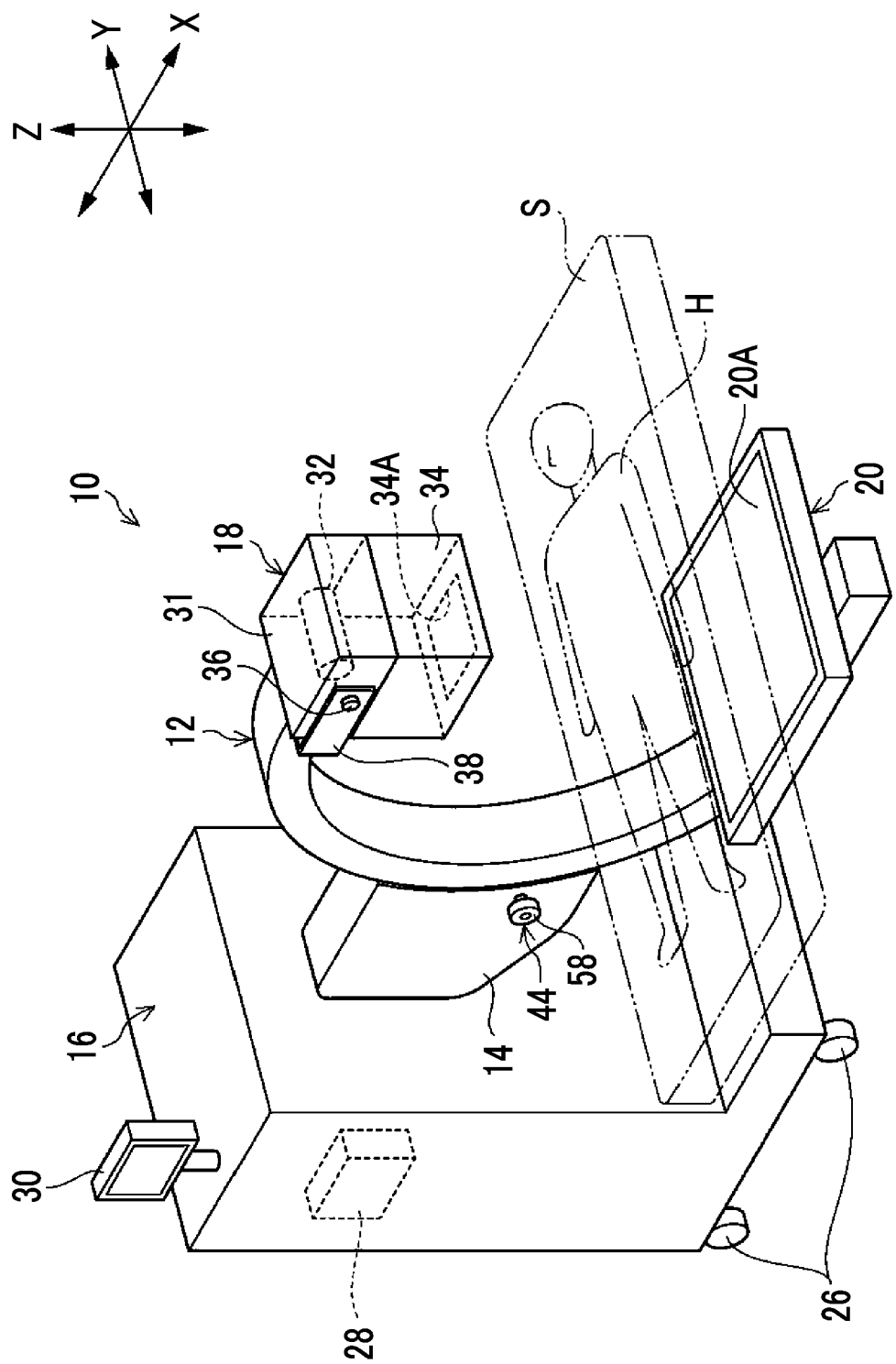
FIG. 1 is an overall perspective view illustrating a radiography apparatus according to a first embodiment.

Hereinafter, radiography apparatuses according to first and second embodiments of the present disclosure will be sequentially described with reference to the drawings. In the drawings, an arrow X indicates the front-rear direction of the radiography apparatus, an arrow Y indicates the width direction of the radiography apparatus, and an arrow Z indicates the vertical direction.

First Embodiment

First, a radiography apparatus according to the first embodiment of the present disclosure will be described with reference to FIGS. 1 to 8.

Overall Configuration of Radiography Apparatus

A radiography apparatus 10 according to this embodiment illustrated in FIG. 1 is an apparatus that captures a radiographic image of a subject H. The radiography apparatus 10 can capture, for example, moving images and still images of the subject H. The capture of the moving image is performed, for example, in a case in which a treatment target part of the subject H is displayed as a moving image during surgery (also referred to as fluoroscopy). In the capture of the moving image, for example, the moving image of the subject H is displayed on a monitor (not illustrated) that is provided separately from the radiography apparatus 10. Of course, data of the captured moving image may be stored in a memory of the radiography apparatus 10. In addition, in the case of the capture of the still image, the captured still image may be displayed on the monitor or may be stored in the memory of the radiography apparatus 10.

As illustrated in FIG. 1, the radiography apparatus 10 includes an arm 12 (referred to as a C-arm or the like) having a C-shape (an arc shape) in a side view and a main body 16 to which a connection portion 14 is attached. Hereinafter, it is assumed that the side of the radiography apparatus 10 on which the arm 12 is provided is the front side of the radiography apparatus 10 and the side on which the main body 16 is provided is the rear side of the radiography apparatus 10.

Configuration of Arm

The arm 12 has two ends. An irradiation unit 18 is provided at one end of the arm 12 and an image receiving unit 20 is provided at the other end. The arm 12 can hold the irradiation unit 18 and the image receiving unit 20 in a posture in which they face each other. A space, into which the subject H and a bed S on which the subject H lies supine can be inserted, is ensured between the irradiation unit 18 and the image receiving unit 20. In the following description, in some cases, in a side view of the arm 12 (as viewed from the Y direction in FIG. 1), a direction in which the irradiation unit 18 and the image receiving unit 20 are provided is referred to as the front side of the arm 12 and the side of the connection portion 14 is referred to as the rear side of the arm 12.

Figure 2A:
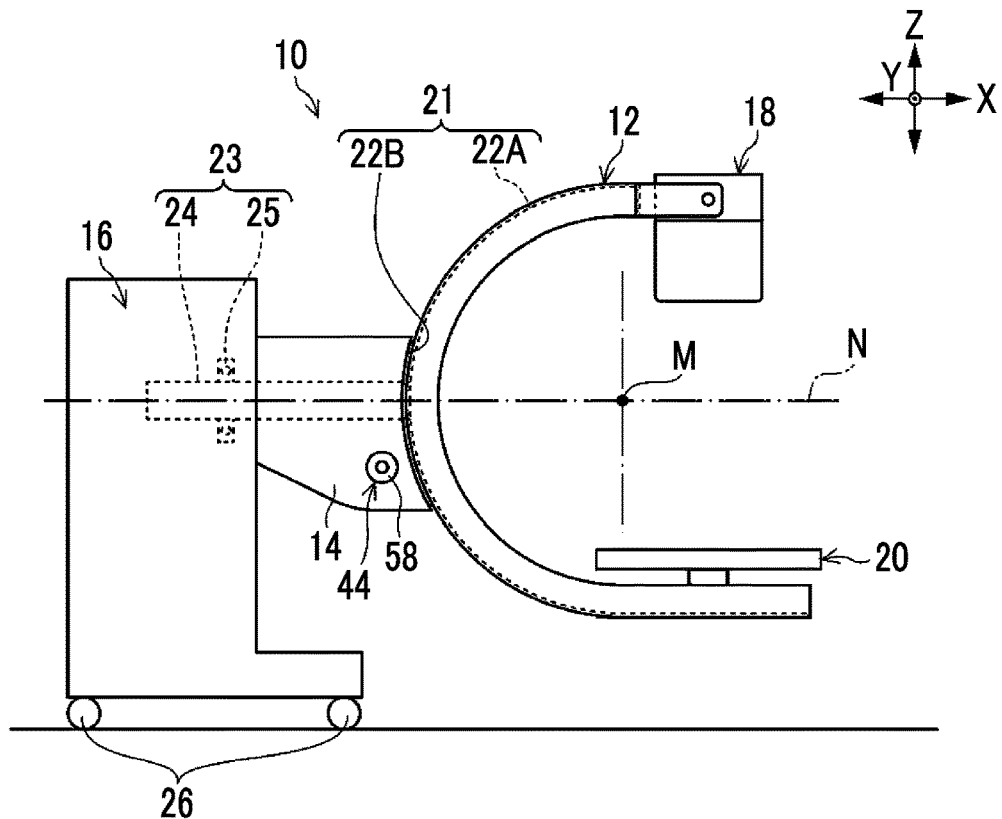
FIG. 2A is a side view illustrating the radiography apparatus according to the first embodiment.

The arm 12 can be rotated by a manual operation. Specifically, as illustrated in FIG. 2A, the arm 12 can be orbitally rotated about an axis line M (an axis line parallel to the Y axis) with respect to the connection portion 14 by a first rotation mechanism 21 which is an example of a displacement mechanism. Further, the arm 12 can be rotated about an axis line N (an axis line parallel to the X-axis) with respect to the main body 16 by a second rotation mechanism 23 which is an example of the displacement mechanism. In this embodiment, the connection portion 14 or the main body 16 corresponds to a "support portion" that supports the arm 12.

Further, the connection portion 14 is provided with an operation handle 44. The operation handle 44 is an operation portion for operating the arm 12. For the operation of the arm 12, basically, the arm 12 is directly operated. However, in this embodiment, the orbital rotation of the arm 12 can be performed using the operation handle 44. The operation handle 44 will be described in detail below.

The first rotation mechanism 21 comprises a track portion 22B that is provided in the connection portion 14 and a fitting portion 22A that is formed on an outer peripheral surface of the arm 12 and is fitted to the track portion 22B. The first rotation mechanism 21 further comprises a pulley shaft 48 (see FIG. 6) as a first rotation shaft which will be described below.

Figure 5:
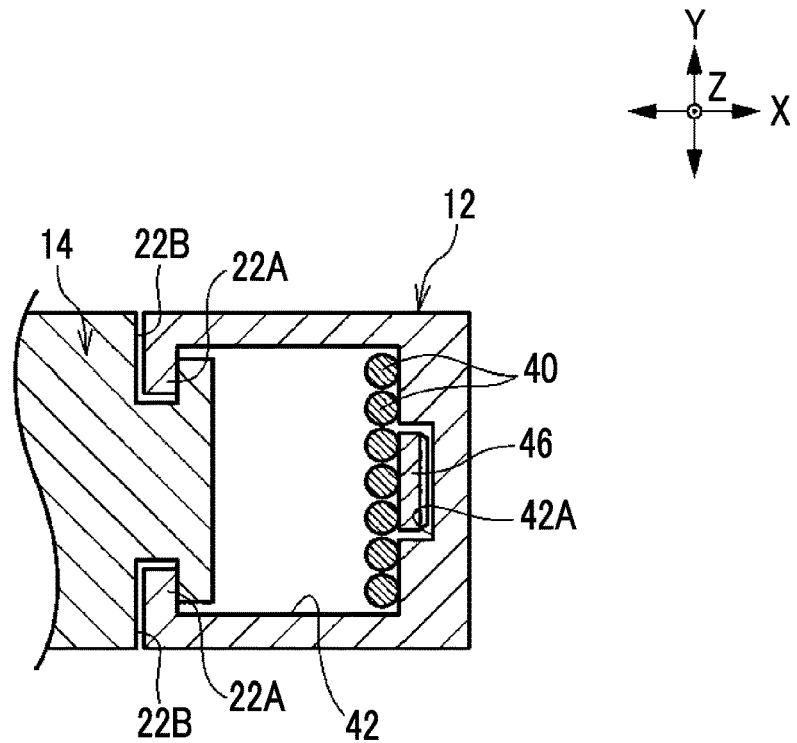
FIG. 5 is a cross-sectional view taken along the line A-A of FIG. 4.

The fitting portion 22A has an arc shape following the shape of the arm 12. The track portion 22B has an arc shape that has the same radius as the arc of the arm 12 and supports the arm 12 so as to be movable along the arc shape. As illustrated in FIG. 5, the track portion 22B has, for example, a groove shape and the fitting portion 22A having a convex shape is fitted to the track portion 22B. A roller (not illustrated) that assists the sliding of the fitting portion 22A with respect to the track portion 22B is interposed between the track portion 22B and the fitting portion 22A.

The fitting portion 22A formed in the arm 12 slides along the track portion 22B formed in the support portion 14 such that the arm 12 can be orbitally rotated about the axis line M at the center of the arc of the arm 12 as a rotation center with respect to the connection portion 14 and the main body 16.

Figure 2B:
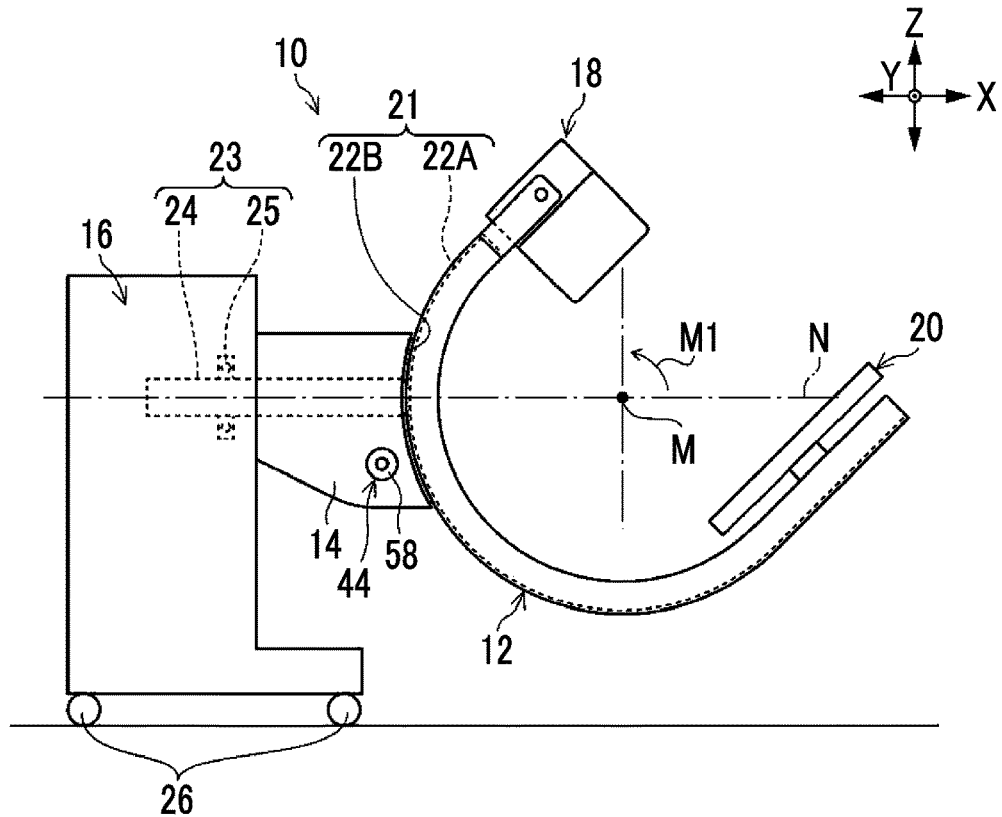
FIG. 2B is a side view illustrating a state in which an arm of the radiography apparatus illustrated in FIG. 2A is rotated in the direction of an arrow M1.
Figure 2C:
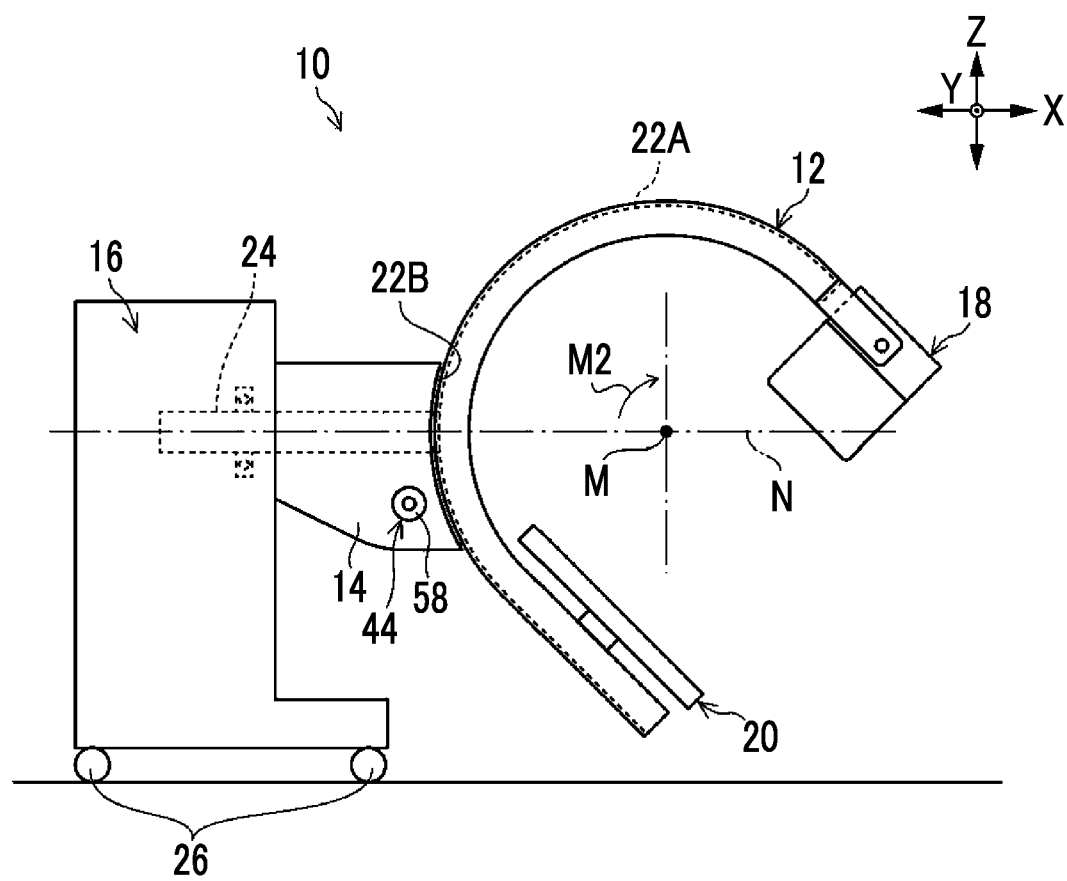
FIG. 2C is a side view illustrating a state in which the arm of the radiography apparatus illustrated in FIG. 2A is rotated in the direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, it is possible to rotate the irradiation unit 18 and the image receiving unit 20 provided at both ends of the arm 12 about the body axis (an axis parallel to the Y axis) of the subject H (see FIG. 1).

As illustrated in FIG. 2A, the second rotation mechanism 23 comprises a support shaft 24 as a second rotation shaft, one end of which is fixed to the arm 12, and a bearing 25 which is provided in the main body 16. The support shaft 24 extends in the front-rear direction (X direction) of the radiography apparatus 10 and has the other end that is supported by the main body 16 through the bearing 25.

Figure 3A:
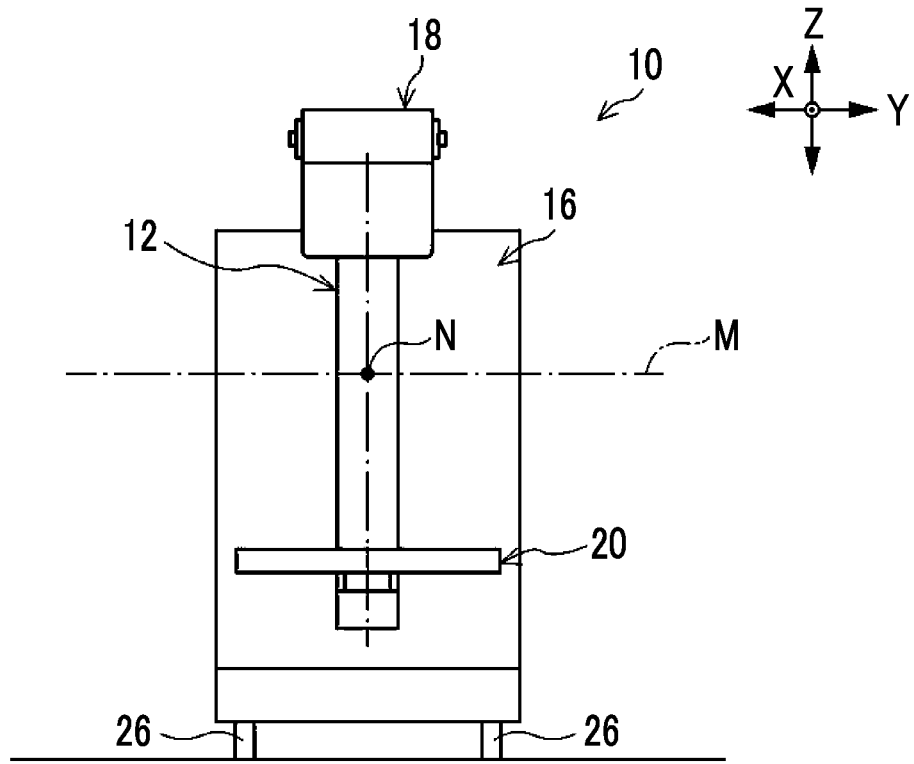
FIG. 3A is a front view illustrating the radiography apparatus according to the first embodiment.
Figure 3B:
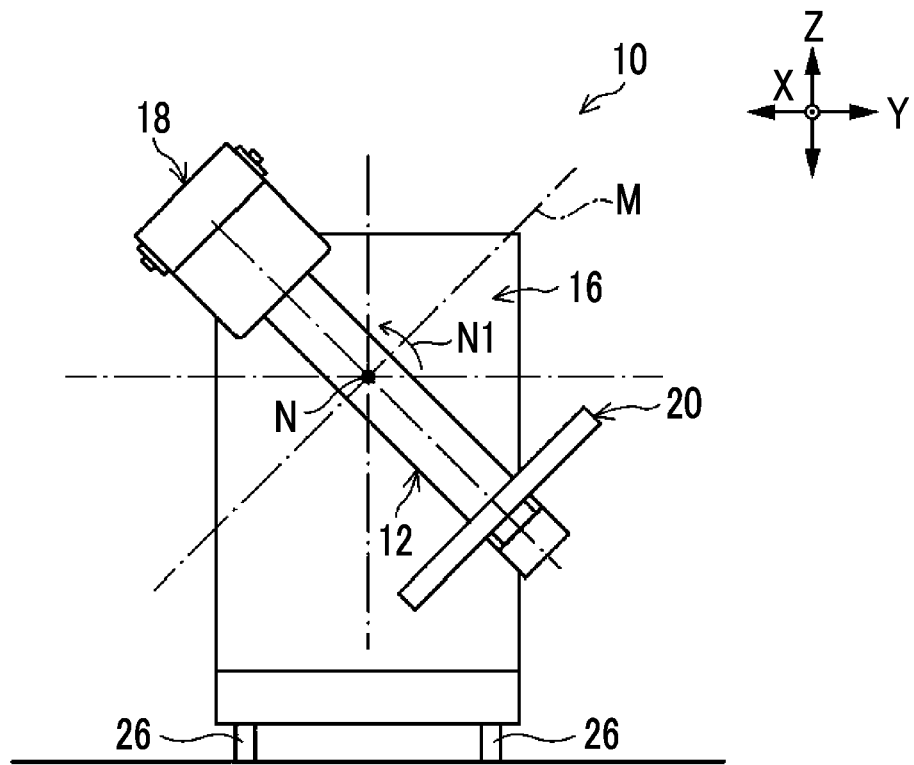
FIG. 3B is a front view illustrating a state in which the arm of the radiography apparatus illustrated in FIG. 3A is rotated in the direction of an arrow N1.
Figure 3C:
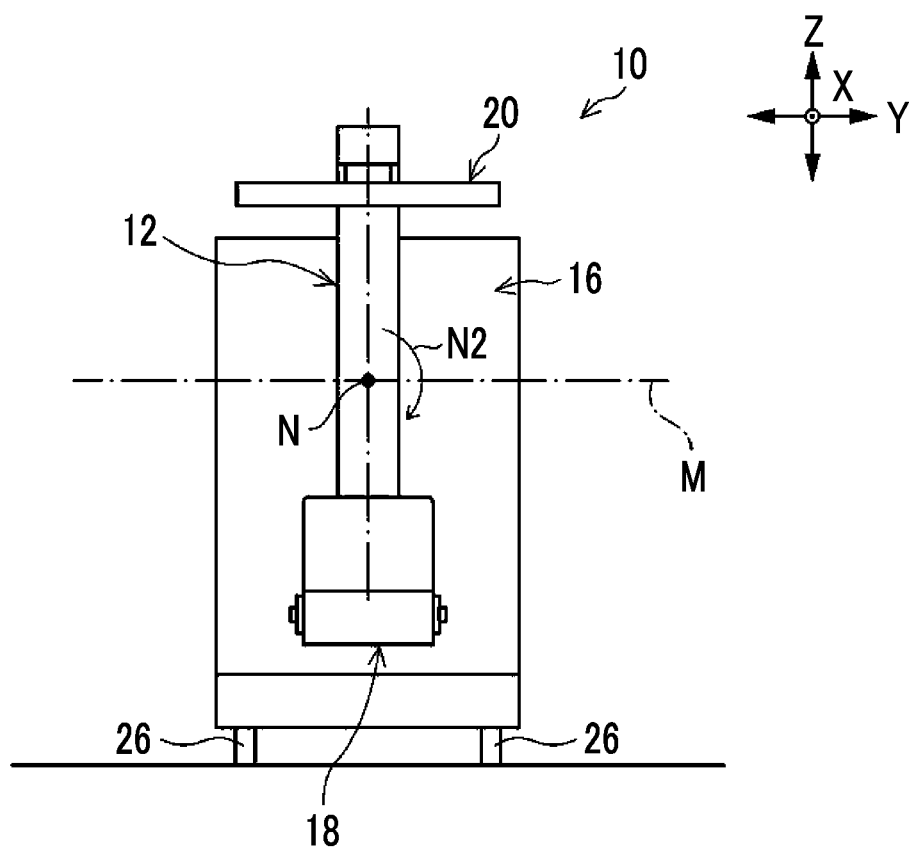
FIG. 3C is a front view illustrating a state in which the arm of the radiography apparatus illustrated in FIG. 3A is rotated 180° in the direction of an arrow N2.

The support shaft 24 is rotated about the axis line N with respect to the bearing 25 such that the arm 12 and the connection portion 14 are rotatable about the axis line N of the support shaft 24 as a rotation center with respect to the main body 16 as illustrated in FIGS. 3A to 3C.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction).

Here, the posture of the arm 12 in which the irradiation unit 18 is disposed above the image receiving unit 20 as illustrated in FIG. 3A is also referred to as an overtube posture since a radiation tube 32 (see FIG. 1) included in the irradiation unit 18 is located above the subject H. In contrast, the posture of the arm 12 in which the irradiation unit 18 is disposed below the image receiving unit 20 illustrated in FIG. 3C is referred to as an undertube posture since the radiation tube 32 is located below the subject H.

In the overtube posture, it is possible to increase a distance between the irradiation unit 18 and the subject H (see FIG. 1) and thus to capture an image of a relatively wide region, as compared to the undertube posture. Therefore, the overtube posture is mainly used to capture the still image of the subject H. In contrast, in the undertube posture, since the radiation emitted from the irradiation unit 18 is partially shielded by, for example, the bed S, it is possible to reduce the amount of radiation exposure of a surgeon or an operator (not illustrated) around the subject H (see FIG. 1). Therefore, the undertube posture is used for the capture of the moving image of the subject H in which radiation is continuously emitted.

Configuration of Main Body

As illustrated in FIG. 1, a plurality of casters 26 are attached to a lower portion of the main body 16 of the radiography apparatus 10 and the operator can push the radiography apparatus 10 with hands to move the radiography apparatus 10 into, for example, an operating room or a hospital ward. That is, the radiography apparatus 10 according to this embodiment is a mobile type.

Further, the main body 16 includes a control unit 28 that controls each unit of the radiography apparatus 10, such as the irradiation unit 18, and an operation panel 30 that is, for example, a touch panel type. In addition, the main body 16 comprises various switches (not illustrated) including, for example, a power switch of the radiography apparatus 10, a power supply circuit that supplies power to each unit of the radiography apparatus 10, and a battery.

The operation panel 30 functions as an operation unit that inputs an operation command to each unit of the radiography apparatus 10 to operate each unit and a display unit that displays various kinds of information, such as a warning message and a radiographic image output from the image receiving unit 20.

Configuration of Control Unit

The control unit 28 transmits a control signal to the radiation tube 32 of the irradiation unit 18, which will be described below, to control, for example, the tube voltage, tube current, and irradiation time of radiation of the radiation tube 32. The tube voltage is controlled to control the energy of radiation and the tube current and the irradiation time are controlled to control the dose of radiation. In practice, since a high voltage is applied to the radiation tube 32, the control unit 28 controls the radiation tube 32 through a high-voltage generation device (not illustrated). In imaging, imaging conditions including, for example, the tube voltage, the tube current, and the irradiation time are set through the operation panel 30. The control unit 28 operates the irradiation unit 18 on the basis of the set imaging conditions.

The control unit 28 directs the irradiation unit 18 to perform moving image capture irradiation in which the irradiation unit 18 continuously emits radiation such that a moving image of the subject H can be captured. In a case in which a moving image is captured, the control unit 28 operates a detector of the image receiving unit 20 which will be described below in synchronization with the moving image capture irradiation by the irradiation unit 18. In the case of the capture of a moving image, basically, the irradiation time is not set as the imaging condition and commands to start and end the capture of a moving image are input through the operation panel 30. In a case in which the command to start the capture of a moving image is input, the control unit 28 directs the irradiation unit 18 to start the emission of radiation under preset imaging conditions.

In the capture of a moving image, the detector repeats an image detection operation at a preset frame rate while the moving image capture irradiation is performed. The image output by the detector is transmitted to the control unit 28. The control unit 28 sequentially outputs the received images to a monitor (not illustrated). Therefore, the moving image of the subject H is displayed on the monitor.

In addition, the control unit 28 directs the irradiation unit 18 to perform still image capture irradiation in which the irradiation unit 18 emits radiation for a shorter time than in the moving image capture irradiation such that a still image of the subject H can be captured.

In the capture of a still image, the control unit 28 operates the detector of the image receiving unit 20 in synchronization with the irradiation timing in the still image capture irradiation by the irradiation unit 18. For example, a command to capture a still image is input through an irradiation switch (not illustrated) that is connected to the control unit 28. In the capture of a still image, the irradiation time is, for example, in the order of several tens of milliseconds to several hundreds of milliseconds. In a case in which a command to capture a still image is input, the control unit 28 operates the irradiation unit 18 on the basis of preset imaging conditions. In the capture of a still image, since the irradiation time is set in the imaging conditions, the irradiation by the irradiation unit 18 ends in a case in which the set irradiation time elapses.

In a case in which the irradiation ends, the detector starts to output the detected image. The image output by the detector is transmitted to the control unit 28. The control unit 28 stores data of the still image in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after imaging.

Configuration of Irradiation Unit

The irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is a focus where radiation is emitted.

The irradiation field limiter 34 is provided below the radiation source 31. The irradiation field limiter 34 (also referred to as a collimator or the like) has a rectangular irradiation opening 34A. The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates (not illustrated) that shield radiation. In each of the four shielding plates, each side corresponds to each side of the irradiation opening 34A and defines the irradiation opening 34A. The position of the shielding plates is changed to adjust the opening area of the irradiation opening 34A and the irradiation field of the radiation emitted from the irradiation unit 18 is changed.

Further, the irradiation unit 18 can be rotated about an axis line of a rotation shaft 36 that extends in the width direction (the Y direction in FIG. 1) of the radiography apparatus 10 as a rotation center with respect to the arm 12. Specifically, a pair of attachment plates 38 (one attachment plate is illustrated in FIG. 1) are fixed to one end of the arm 12.

The pair of attachment plates 38 are disposed such that both sides of the irradiation unit 18 in the width direction are interposed therebetween and are connected to both side surfaces of the irradiation unit 18 in the width direction. The rotation shafts 36 are provided on each of the side surfaces of the irradiation unit 18 facing the attachment plates 38 so as to protrude. The rotation shafts 36 are supported by the pair of attachment plates 38 through bearings (not illustrated). Therefore, the irradiation unit 18 can be rotated about the axis line of the rotation shaft 36 as the rotation center with respect to the attachment plates 38 and the orientation of the irradiation opening 34A of the irradiation unit 18 can be changed in the front-rear direction of the arm 12. The orientation of the irradiation opening 34A is changed to change the irradiation direction of radiation.

The irradiation unit 18 is connected to one end of each of a plurality of cables 40 including a signal line for transmitting a control signal and a power line for supplying power. As illustrated in FIG. 5, the cables 40 are provided in a hollow portion 42 that is formed in the arm 12 and extend along the arm 12. The other end of the cable 40 is connected to, for example, the control unit 28 and a power supply circuit (not illustrated) of the main body 16 illustrated in FIG. 1.

Configuration of Image Receiving Unit

As illustrated in FIG. 1, the image receiving unit 20 is provided at the other end of the arm 12 which is a position facing the irradiation unit 18. The image receiving unit 20 comprises a detector provided in a housing. The image receiving unit 20 has an image receiving surface 20A that receives the radiation which has been emitted from the irradiation unit 18 and then transmitted through the subject H. The radiation carrying the information of the subject H is incident on the image receiving surface 20A.

The detector is, for example, a flat panel detector (FPD) of a digital radiography (DR) type. The FPD has a detection surface in which a plurality of pixels are two-dimensionally arranged and a thin film transistor (TFT) panel (not illustrated) for driving the pixels. Radiation is incident on the detection surface of the detector through the image receiving surface 20A. The detector converts the incident radiation into an electric signal and outputs a radiographic image indicating the subject H on the basis of the converted electric signal. For example, the detector is an indirect conversion type that converts radiation into visible light using a scintillator and converts the converted visible light into an electric signal. In addition, the detector may be a direct conversion type that directly converts radiation into an electric signal. Further, the image receiving unit 20 may have, for example, a configuration in which an image intensifier (I.I) and a camera are combined other than the configuration using the FPD.

Further, the image receiving unit 20 is connected to, for example, the control unit 28 and the power supply circuit (not illustrated) of the main body 16 by a cable (not illustrated) including a signal line for transmitting a control signal and a power line for supplying power.

Configuration of Operation Handle

Figure 4:
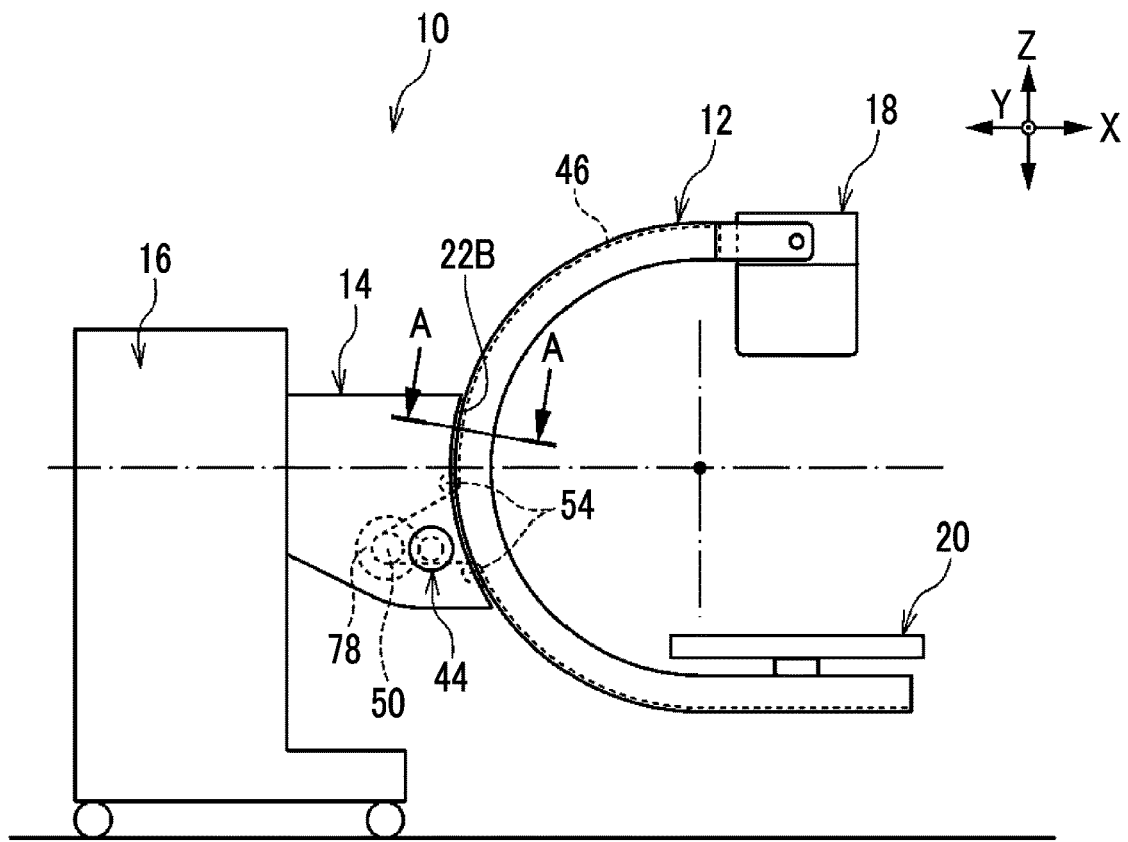
FIG. 4 is an overall side view illustrating an operation handle of the radiography apparatus according to the first embodiment.

As illustrated in FIG. 4, the operation handle 44 is provided in the connection portion 14 of the radiography apparatus 10 independently of the arm 12 and is manually operated to input an operation force for rotating the arm 12 to the pulley shaft 48 (see FIG. 6) forming the first rotation mechanism 21.

Specifically, both ends of a belt 46 are fixed to both ends of the arm 12, respectively. The arm 12 is a hollow cylindrical body. As illustrated in FIG. 5, the belt 46 and the cables 40 are provided in the hollow portion 42 of the arm 12. In the hollow portion 42, a groove 42A that extends along the arc of the arm 12 is formed in the front inner surface of the arm 12. The belt 46 extends along the arc of the arm 12 while being accommodated in the groove 42A. Therefore, it is possible to suppress interference between the cables 40 and the belt 46 in the hollow portion 42 of the arm 12.

Figure 6:
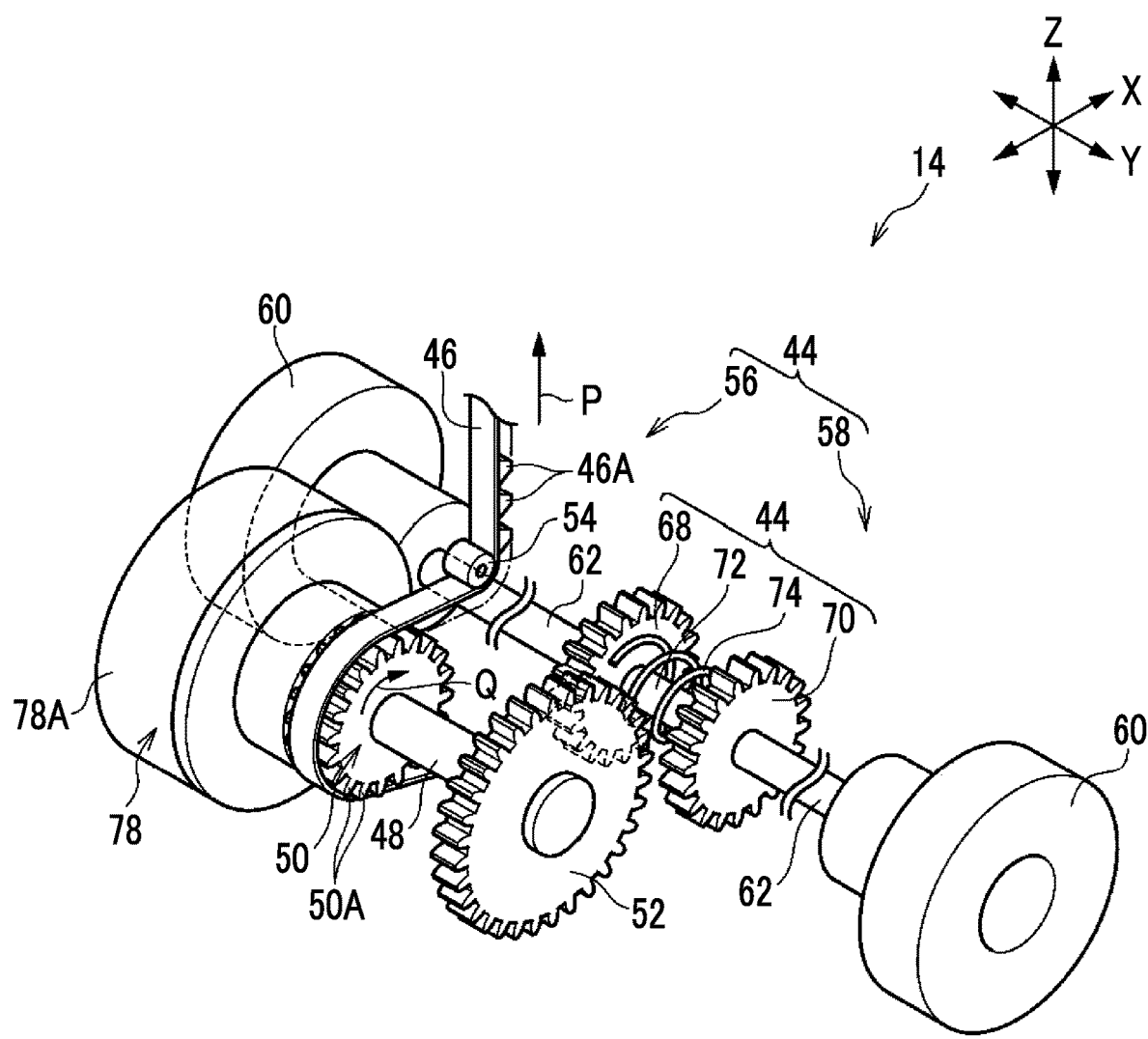
FIG. 6 is a perspective view illustrating the operation handles of the radiography apparatus according to the first embodiment.
Figure 7:
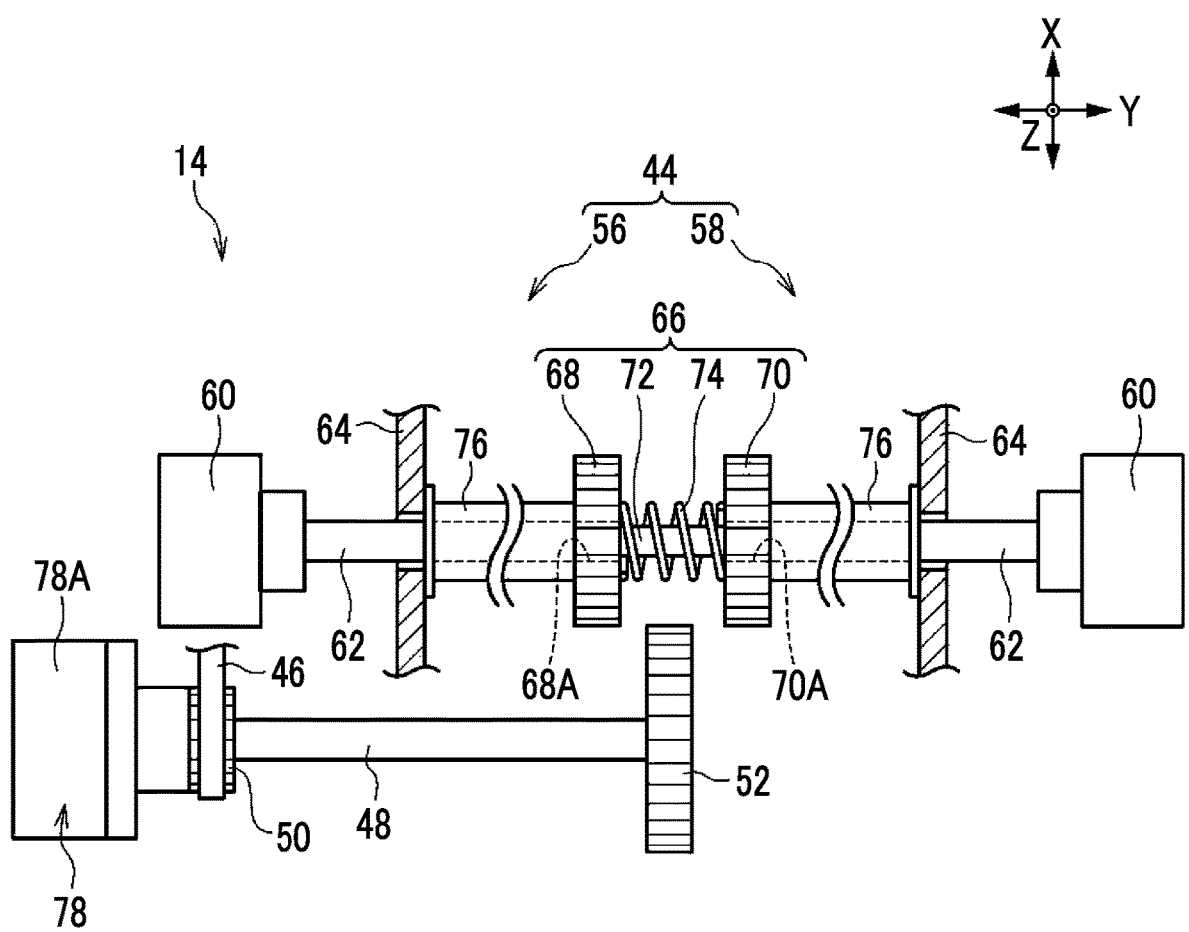
FIG. 7 is a plan view illustrating the operation handles illustrated in FIG. 6.

As illustrated in FIGS. 6 and 7, the connection portion 14 is provided with the pulley shaft 48 forming the first rotation mechanism 21. The pulley shaft 48 is supported by the connection portion 14 through a bearing (not illustrated) so as to be rotatable. A pulley 50 and a main gear 52 are fixed to the pulley shaft 48 so as to be coaxially rotatable and the belt 46 is wound around the pulley 50.

The belt 46 is a timing belt having a plurality of teeth 46A formed thereon. The pulley 50 is a timing pulley having a plurality of grooves 50A formed in an outer peripheral surface. The teeth 46A of the belt 46 are engaged with the grooves 50A of the pulley 50 such that the belt 46 and the pulley 50 are operatively associated with each other.

Further, as illustrated in FIG. 4, idlers 54 are provided above and below the pulley 50 in the vertical direction (Z direction) in the connection portion 14, respectively. The belt 46 is guided by a pair of idlers 54 while being kept at a predetermined tension and is wound around the pulley 50.

In a case in which the arm 12 is orbitally rotated with respect to the track portion 22B, the belt 46 follows the movement of the arm 12. For example, in a case in which one end of the arm 12 is moved in a direction in which it becomes further away from the connection portion 14 (track portion 22B), the belt 46 is moved in the direction of an arrow P in FIG. 6, that is, in a direction in which the one end becomes further away from the connection portion 14. In this case, the pulley 50 engaged with the belt 46 is also rotated in the direction of an arrow Q (clockwise in FIG. 6) following the movement of the belt 46.

As illustrated in FIGS. 6 and 7, the operation handle 44 includes a first operation handle 56 and a second operation handle 58. Specifically, the first and second operation handles 56 and 58 have the same configuration and comprise a grip portion 60 and a cylindrical handle shaft 62 that is fixed to the grip portion 60 so as to be coaxially rotatable.

The grip portion 60 is a portion which the operator grips with hands to operate the operation handle 44 (the first and second operation handles 56 and 58). In this embodiment, the grip portion 60 has a cylindrical shape that has a larger outer diameter than the handle shaft 62.

The handle shaft 62 is disposed in parallel to the pulley shaft 48 forming the first rotation mechanism 21 and is supported by the connection portion 14 so as to be rotatable and movable in the axial direction. The handle shaft 62 of the first operation handle 56 and the handle shaft 62 of the second operation handle 58 are disposed on the same axis line, and the other ends thereof in the axial direction face each other.

As illustrated in FIG. 7, one end of each of the handle shafts 62 of the first operation handle 56 and the second operation handle 58 in the axial direction is exposed from a side wall 64 of the connection portion 14 to the outside of the connection portion 14. The grip portion 60 is provided at the one end of the handle shaft 62 in the axial direction. That is, the grip portion 60 of the first operation handle 56 and the grip portion 60 of the second operation handle 58 are provided on both side surfaces of the connection portion 14 so as to protrude. Therefore, the operator can grip the grip portions 60 from both sides of the connection portion 14 and operate the first operation handle 56 and the second operation handle 58.

A switching mechanism 66 for switching between a valid state in which the input of an operation force from the operation handle 44 to the pulley shaft 48 of the first rotation mechanism 21 is validated and an invalid state in which the input is invalidated is provided at the other end of the handle shaft 62 in the axial direction which is located inside the connection portion 14.

The switching mechanism 66 includes a first gear 68, a second gear 70, and a shaft 72 and a biasing member 74 that are provided between the first gear 68 and the second gear 70. The first gear 68 is fixed to the other end of the handle shaft 62 of the first operation handle 56 in the axial direction so as to be coaxially rotatable. The second gear 70 is fixed to the other end of the handle shaft 62 of the second operation handle 58 in the axial direction so as to be coaxially rotatable.

The first and second gears 68 and 70 face each other with a gap therebetween in the axial direction of the handle shaft 62. The main gear 52 fixed to the pulley shaft 48 is located between the first gear 68 and the second gear 70 in the axial direction of the handle shaft 62. In a case in which the first gear 68 and the second gear 70 are moved to the other end of the handle shaft 62 in the axial direction, the main gear 52 is engaged with the first gear 68 or the second gear 70.

Further, spacers 76 are provided between the first gear 68 and the side wall 64 of the connection portion 14 and between the second gear 70 and the side wall 64 of the connection portion 14. The spacer 76 is a cylindrical member into which the handle shaft 62 is inserted. The spacer 76 regulates the movement of the first gear 68 and the second gear 70 to the side wall 64, that is, the movement of the first gear 68 and the second gear 70 to the ends of the handle shaft 62 in the axial direction. One end of the spacer 76 is fixed to the inner surface of the side wall 64.

The shaft 72 has an outer diameter that is smaller than an inner diameter of a shaft hole 68A of the first gear 68 and an inner diameter of a shaft hole 70A of the second gear 70 and is inserted into the shaft hole 68A of the first gear 68 and the shaft hole 70A of the second gear 70. Further, both ends of the shaft 72 in the axial direction are located inside the handle shaft 62 of the first operation handle 56 and the handle shaft 62 of the second operation handle 58, respectively.

The biasing member 74 is, for example, a coil spring that is wound around the outer peripheral surface of the shaft 72. The biasing member 74 has one end that comes into contact with the first gear 68 and the other end that comes into contact with the second gear 70 and biases the first gear 68 and the second gear 70 in a direction in which they are separated from each other, that is, to one end of the handle shaft 62 in the axial direction.

Figure 8A:
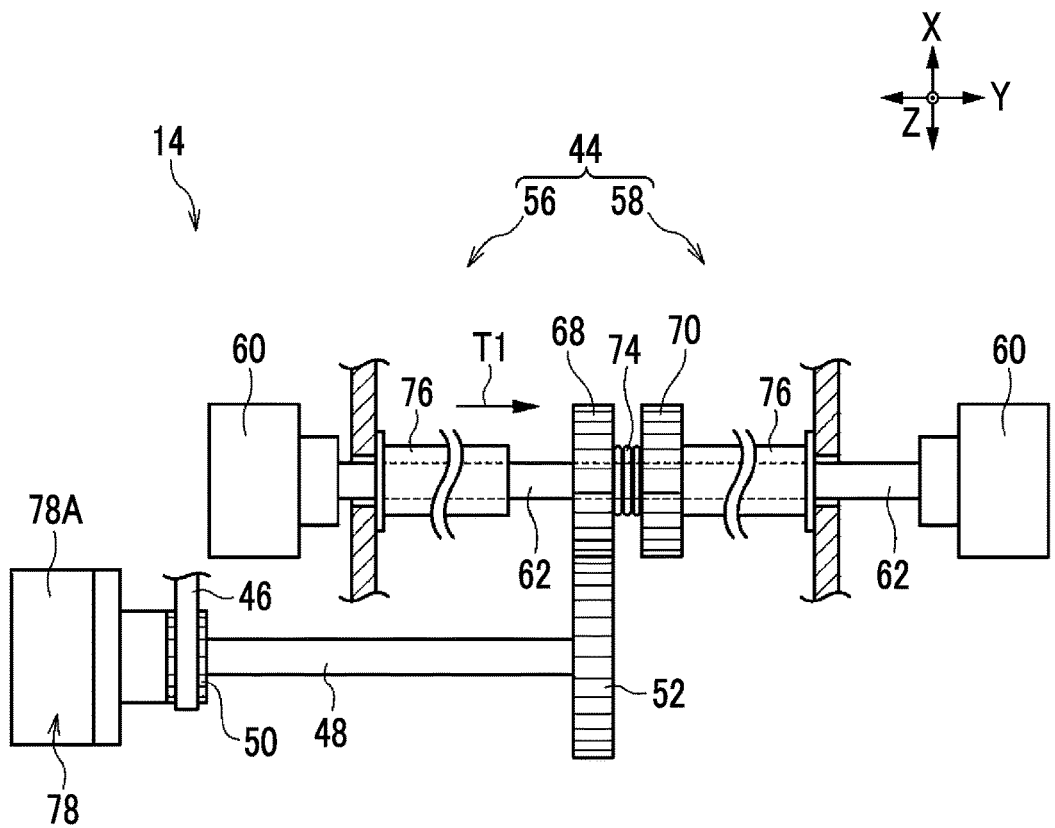
FIG. 8A is an operation diagram illustrating a state in which one of the operation handles illustrated in FIG. 7 is slid in an axial direction.

In a case in which the first operation handle 56 is operated, the operator grips the grip portion 60 protruding from the side wall 64 of the connection portion 14 with the hand and pushes the grip portion 60 to the inside of the connection portion 14, that is, to the other end of the handle shaft 62 in the axial direction (the direction of an arrow T1 in FIG. 8A) as illustrated in FIG. 8A. In this case, the first gear 68 fixed to the other end of the handle shaft 62 in the axial direction is biased to one end of the handle shaft 62 in the axial direction by the biasing member 74. Therefore, the operator slides the first operation handle 56 in the axial direction against the biasing force of the biasing member 74.

In a case in which the grip portion 60 of the first operation handle 56 is pushed, the handle shaft 62 is moved to the other end in the axial direction, and the first gear 68 fixed to the other end of the handle shaft 62 in the axial direction is also moved to the other end in the axial direction. In this case, since the movement of the second gear 70 of the second operation handle 58 to the one end of the handle shaft 62 in the axial direction is regulated by the spacer 76, the second gear 70 is not moved in the axial direction of the handle shaft 62 and the first gear 68 approaches the second gear 70 against the biasing force of the biasing member 74.

Therefore, the main gear 52 disposed between the first gear 68 and the second gear 70 is engaged with the first gear 68. In a case in which the main gear 52 and the first gear 68 are engaged with each other, the pulley shaft 48 and the handle shaft 62 are connected and the first operation handle 56 is switched to the valid state in which the input of the operation force to the first rotation mechanism 21 (see FIG. 2A) is valid.

In a case in which the grip portion 60 is rotated with the main gear 52 engaged with the first gear 68, the handle shaft 62 and the first gear 68 are rotated with the rotation of the grip portion 60 and the main gear 52 engaged with the first gear 68 is rotated. Then, as the main gear 52 is rotated, the pulley shaft 48 and the pulley 50 fixed to the pulley shaft 48 are rotated.

Since the belt 46 fixed to both ends of the arm 12 illustrated in FIG. 4 is wound around the pulley 50, the arm 12 is orbitally rotated as the pulley 50 is rotated. That is, the first operation handle 56 can be operated to rotate the arm 12.

Figure 8B:
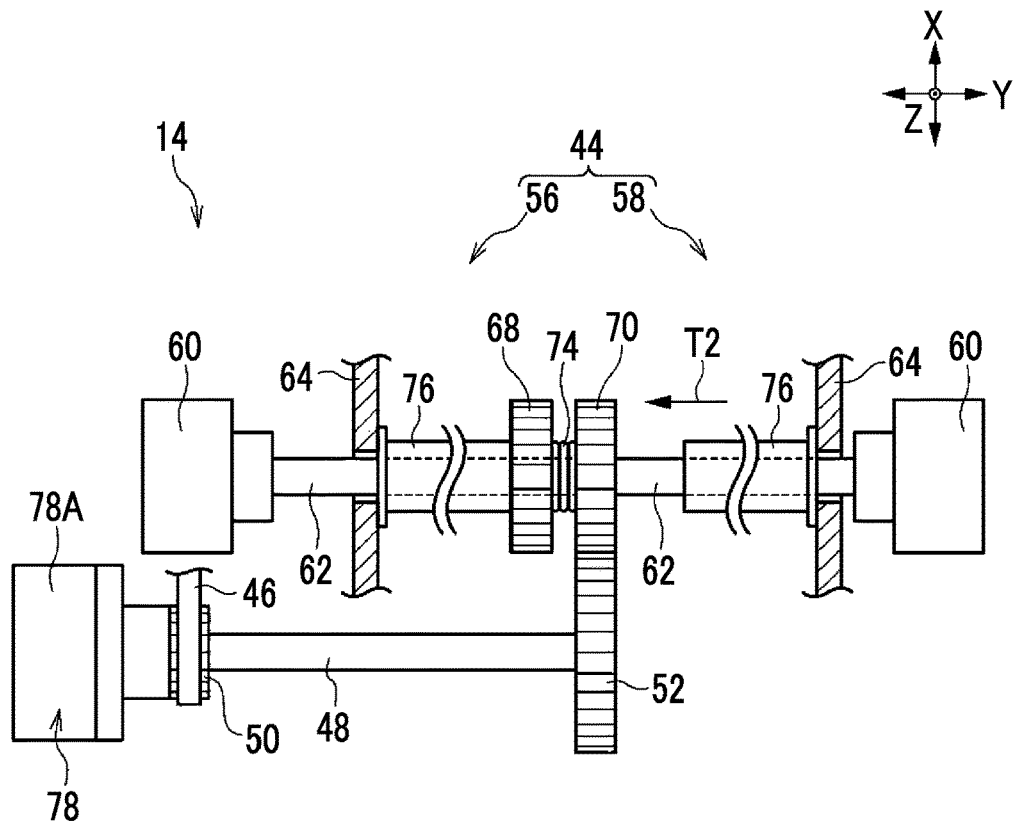
FIG. 8B is an operation diagram illustrating a state in which the other of the operation handles illustrated in FIG. 7 is slid in the axial direction.

In a case in which the second operation handle 58 is operated, the grip portion 60 of the second operation handle 58 is pushed to slide the second operation handle 58 in the axial direction as in the case of the first operation handle 56. Then, as illustrated in FIG. 8B, the handle shaft 62 and the second gear 70 fixed to the other end of the handle shaft 62 in the axial direction are moved to the other end in the axial direction (the direction of an arrow T2 in FIG. 8B).

In this case, since the movement of the first gear 68 of the first operation handle 56 to the one end of the handle shaft 62 in the axial direction is regulated by the spacer 76, the first gear 68 is not moved in the axial direction of the handle shaft 62 and the second gear 70 approaches the first gear 68 against the biasing force of the biasing member 74.

Therefore, the main gear 52 disposed between the first gear 68 and the second gear 70 is engaged with the second gear 70. In a case in which the main gear 52 and the second gear 70 are engaged with each other, the pulley shaft 48 and the handle shaft 62 are connected and the second operation handle 58 is switched to the valid state in which the input of the operation force to the first rotation mechanism 21 (see FIG. 2A) is valid.

In a case in which the grip portion 60 is rotated with the main gear 52 engaged with the second gear 70, the handle shaft 62 and the second gear 70 are rotated with the rotation of the grip portion 60 and the main gear 52 engaged with the second gear 70 is rotated. Then, as the main gear 52 is rotated, the pulley shaft 48 and the pulley 50 fixed to the pulley shaft 48 are rotated. As the pulley 50 is rotated, the arm 12 illustrated in FIG. 4 is orbitally rotated. That is, the second operation handle 58 can be operated to rotate the arm 12.

The first operation handle 56 and the second operation handle 58 are biased to one end in the axial direction by the biasing member 74. Therefore, in a case in which the first operation handle 56 and the second operation handle 58 are not operated, that is, in a case in which the grip portion 60 is not pushed, the first gear 68 and the second gear 70 are not engaged with the main gear 52 as illustrated in FIG. 7. As a result, the first operation handle 56 and the second operation handle 58 are switched to the invalid state in which the input of the operation force to the first rotation mechanism 21 (see FIG. 2A) is invalid.

Configuration of Electromagnetic Brake

Further, in this embodiment, in addition to the operation handle 44, an electromagnetic brake 78 that locks the rotation of the arm 12 by the first rotation mechanism 21 is connected to the pulley shaft 48.

The electromagnetic brake 78 is, for example, a non-excitation operation type, locks rotation in a case in which it is not energized, and unlocks rotation in a case in which it is energized. Since the electromagnetic brake 78 of the non-excitation operation type which locks rotation in a case in which it is de-energized is used, the rotation of the arm 12 is locked in a case in which the electromagnetic brake 78 is de-energized due to, for example, a power failure. Therefore, it is possible to suppress the inadvertent rotation of the arm 12.

Specifically, the electromagnetic brake 78 comprises a housing 78A in which an electromagnet (not illustrated) is provided. The pulley shaft 48 is attached to the housing 78A through a rotor (not illustrated) that is provided in the housing 78A. The housing 78A is fixed to the connection portion 14 so as not to be rotatable. The rotor and the pulley shaft 48 are rotatable with respect to the housing 78A.

The electromagnet and the rotor are disposed around the pulley shaft 48 so as to face each other in the axial direction of the pulley shaft 48, which is not illustrated. Further, in the housing 78A, a movable iron piece that is movable in the axial direction of the pulley shaft 48 is provided between the electromagnet and the rotor. The movable iron piece is disposed so as to be separated from the electromagnet and is biased toward the rotor by a biasing member (not illustrated) to press the rotor against the inner wall surface of the housing 78A.

In a case in which the electromagnetic brake 78 is not energized, the movable iron piece presses the rotor against the inner wall surface of the housing 78A so as to come into close contact therewith. Therefore, the rotation of the rotor with respect to the housing 78A is locked. In a case in which the rotation of the rotor with respect to the housing 78A is locked, the rotation of the pulley shaft 48 fixed to the rotor and the pulley 50 fixed to the pulley shaft 48 is locked and the movement of the belt 46 engaged with the pulley 50 is also locked. Since both ends of the belt 46 are fixed to both ends of the arm 12 illustrated FIG. 4, the orbital rotation of the arm 12 with respect to the track portion is locked by the locking of the movement of the belt 46.

In contrast, in a case in which the electromagnetic brake 78 is energized, a magnetic force is generated in the electromagnet provided in the housing 78A and the movable iron piece is attracted to the electromagnet against the biasing force of the biasing member. Therefore, the pressing of the rotor against the inner wall surface of the housing 78A by the movable iron piece is released and the rotor can be rotated with respect to the housing 78A. That is, the rotation of the rotor is unlocked.

Further, in a case in which the rotation of the rotor is unlocked, the rotation of the pulley shaft 48 and the pulley 50 is also unlocked and the belt 46 engaged with the pulley 50 can be moved. Therefore, the orbital rotation of the arm 12 illustrated in FIG. 4 with respect to the track portion is unlocked.

Operation and Effect

The radiography apparatus 10 according to this embodiment comprises the first rotation mechanism 21 (an example of the displacement mechanism) that rotates the arm 12 with respect to the connection portion 14 and the operation handle 44 that is provided independently of the arm 12 and is manually operated to input an operation force for rotating the arm 12 to the first rotation mechanism 21. Therefore, the operation handle 44 makes it possible to manually operate the arm 12 without directly operating the arm 12.

In many cases, the radiography apparatus 10 including the arm 12 that holds the irradiation unit 18 and the image receiving unit 20 is used during surgery. The operation handle 44 is provided independently of the arm 12, which makes it possible to separate an operation part operated by the operator from an operation part operated by the assistant. Therefore, the following method can also be used: the assistant rotates the arm 12 with the operation handle 44 while avoiding the arm 12 contaminated by contact with the operator. The assistant does not directly touch the arm 12 contaminated by, for example, blood, which is hygienic.

In particular, according to this embodiment, the operation handle 44 inputs an operation force to a rotation mechanism (first rotation mechanism 21) that rotates the arm 12. The operations performed during surgery include a slide operation of sliding the arm 12 in the horizontal direction and a rotation operation of rotating the arm 12. It is considered that the rotation operation is more frequently performed than the slide operation. Therefore, the operation handle 44 according to this embodiment is particularly effective in a case in which it is combined with the rotation mechanism (first rotation mechanism 21).

Further, since the arm 12 is displaced through the first rotation mechanism 21, the amount of rotation of the arm 12 can be adjusted more easily than that in a case in which the arm 12 is directly operated. That is, for example, the gear ratio of the first rotation mechanism 21 can be set to adjust the relationship between the amount of rotation of the operation handle 44 and the amount of rotation of the arm 12. Therefore, the setting of reducing the amount of rotation of the arm 12 with respect to the amount of rotation of the operation handle 44 is relatively simple. The operation handle 44 makes it easy to finely adjust the amount of rotation of the arm 12.

According to this embodiment, the arm 12 may not be rotated by an electromotive force, but may be rotated by only a manual operation. Therefore, it is possible to reduce the size and weight of the entire radiography apparatus 10. Further, in the case of the electric operation, it is easy to finely adjust the amount of rotation of the arm 12. However, in the manual operation, it is difficult to perform finely adjust the amount of rotation of the arm 12 in a case in which the arm 12 is directly operated. Therefore, the operation handle 44 according to this embodiment is particularly effective for the radiography apparatus 10 with a small size and weight in which the arm 12 is rotated by only a manual operation.

According to this embodiment, the operation handle 44 (the first operation handle 56 and the second operation handle 58) has the handle shaft 62 that is rotated with the rotation of the operation handle 44. The pulley shaft 48 of the first rotation mechanism 21 and the handle shaft 62 are connected to input the operation force of the operation handle 44 to the first rotation mechanism 21. As such, the pulley shaft 48 of the first rotation mechanism 21 and the handle shaft 62 of the operation handle 44 are connected to obtain a relatively simple configuration.

This embodiment is provided with the switching mechanism 66 for switching between the valid state in which the input of the operation force from the operation handle 44 to the first rotation mechanism 21 is validated and the invalid state in which the input is invalidated. Since the switching mechanism 66 can switch the operative association between the first rotation mechanism 21 and the operation handle 44, it is possible to prevent the operation handle 44 from being rotated with the rotation of the arm 12 in a case in which the arm 12 is directly rotated.

Further, according to this embodiment, the switching mechanism 66 can slide the operation handle 44 (the first operation handle 56 and the second operation handle 58) in the axial direction to switch between the valid state and the invalid state. Therefore, the operative association between the first rotation mechanism 21 and the operation handle 44 can be switched by a simple operation.

In particular, according to this embodiment, the switching mechanism 66 comprises the biasing member 74. The biasing member 74 biases the operation handle 44 in a direction in which the operation handle 44 is switched to the invalid state. Therefore, the operation handle 44 is manually slid in the axial direction against the biasing force of the biasing member 74 such that the operation handle 44 can be switched to the valid state. The operation handle 44 can be switched to the invalid state only by releasing the hand from the operation handle 44.

According to this embodiment, the electromagnetic brake 78 is connected to the first rotation mechanism 21 in addition to the operation handle 44. As such, the electromagnetic brake 78 is connected to the first rotation mechanism 21 to lock the rotation of the arm 12 as necessary. Therefore, it is possible to suppress the inadvertent rotation of the arm 12.

Second Embodiment

Next, a radiography apparatus 100 according to the second embodiment of the present disclosure will be described with reference to FIGS. 9 to 11. In addition, the same configurations as those in the first embodiment are denoted by the same reference numerals and the description thereof will not be repeated. The description is focused on the differences between the first and second embodiments.

In the radiography apparatus 10 according to the first embodiment, the operation handle 44 is connected to the first rotation mechanism 21 that orbitally rotates the arm 12. In contrast, as illustrated in FIG. 9, in the radiography apparatus 100 according to this embodiment, an operation handle 102 is connected to the second rotation mechanism 23 that rotates the arm 12 about the axis.

Specifically, in the main body 16 of the radiography apparatus 100, a main gear 104 is fixed to the outer peripheral surface of the support shaft 24 forming the second rotation mechanism 23 so as to be coaxially rotatable. The operation handle 102 is connected to the main gear 104 through a switching mechanism 106.

Figure 10:
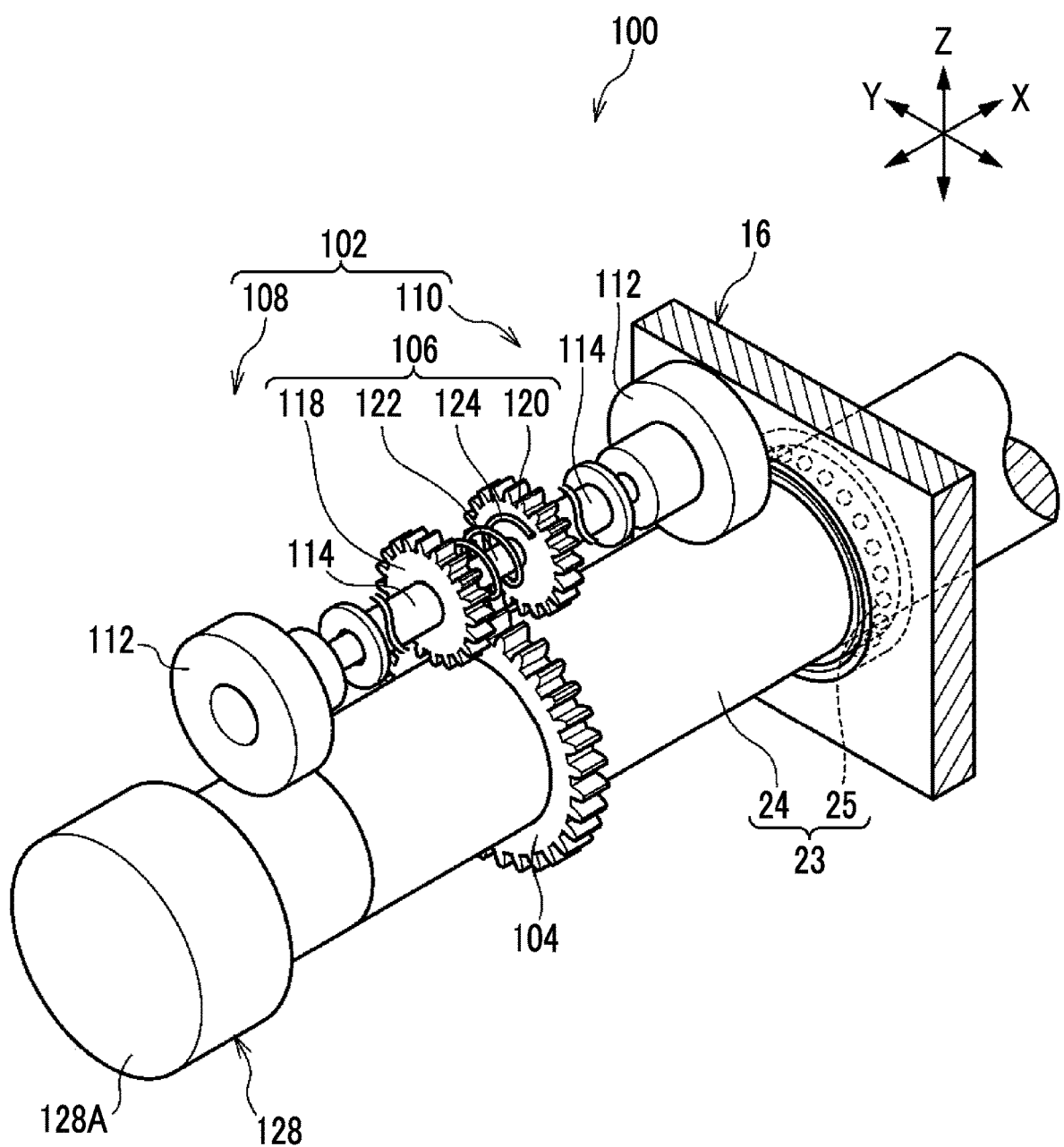
FIG. 10 is a perspective view illustrating the operation handles of the radiography apparatus according to the second embodiment.

As illustrated in FIG. 10, the operation handle 102 includes a first operation handle 108 and a second operation handle 110. The first operation handle 108 and the second operation handle 110 have the same configuration as the first operation handle 56 and the second operation handle 58 according to the first embodiment, respectively, and comprises a grip portion 112 and a handle shaft 114 that is fixed to the grip portion 112 so as to be coaxially rotatable.

The handle shaft 114 is disposed in parallel to the support shaft 24 and is supported by the main body 16 so as to be rotatable and movable in the axial direction. Further, the handle shaft 114 of the first operation handle 108 and the handle shaft 114 of the second operation handle 110 are disposed on the same axis line and the other ends thereof in the axial direction face each other.

Figure 9:
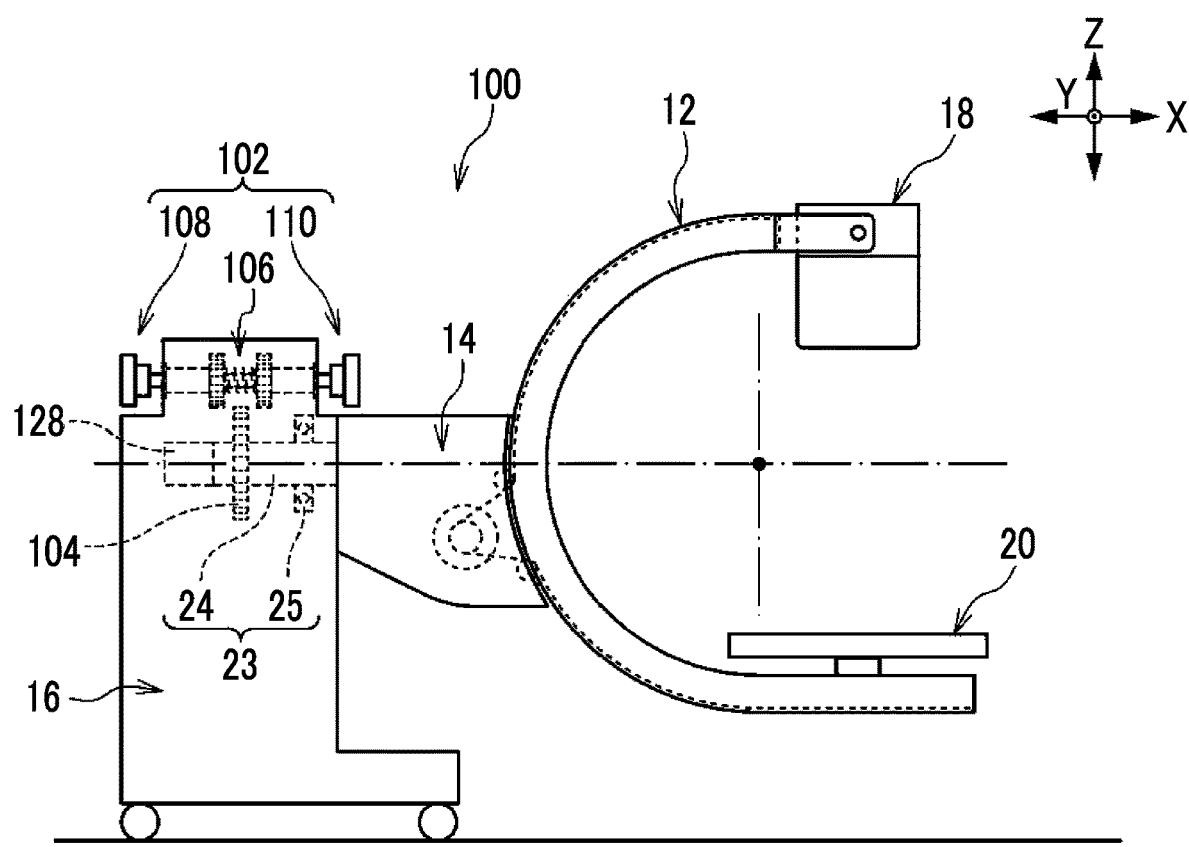
FIG. 9 is an overall side view illustrating an operation handle of a radiography apparatus according to a second embodiment.
Figure 11A:
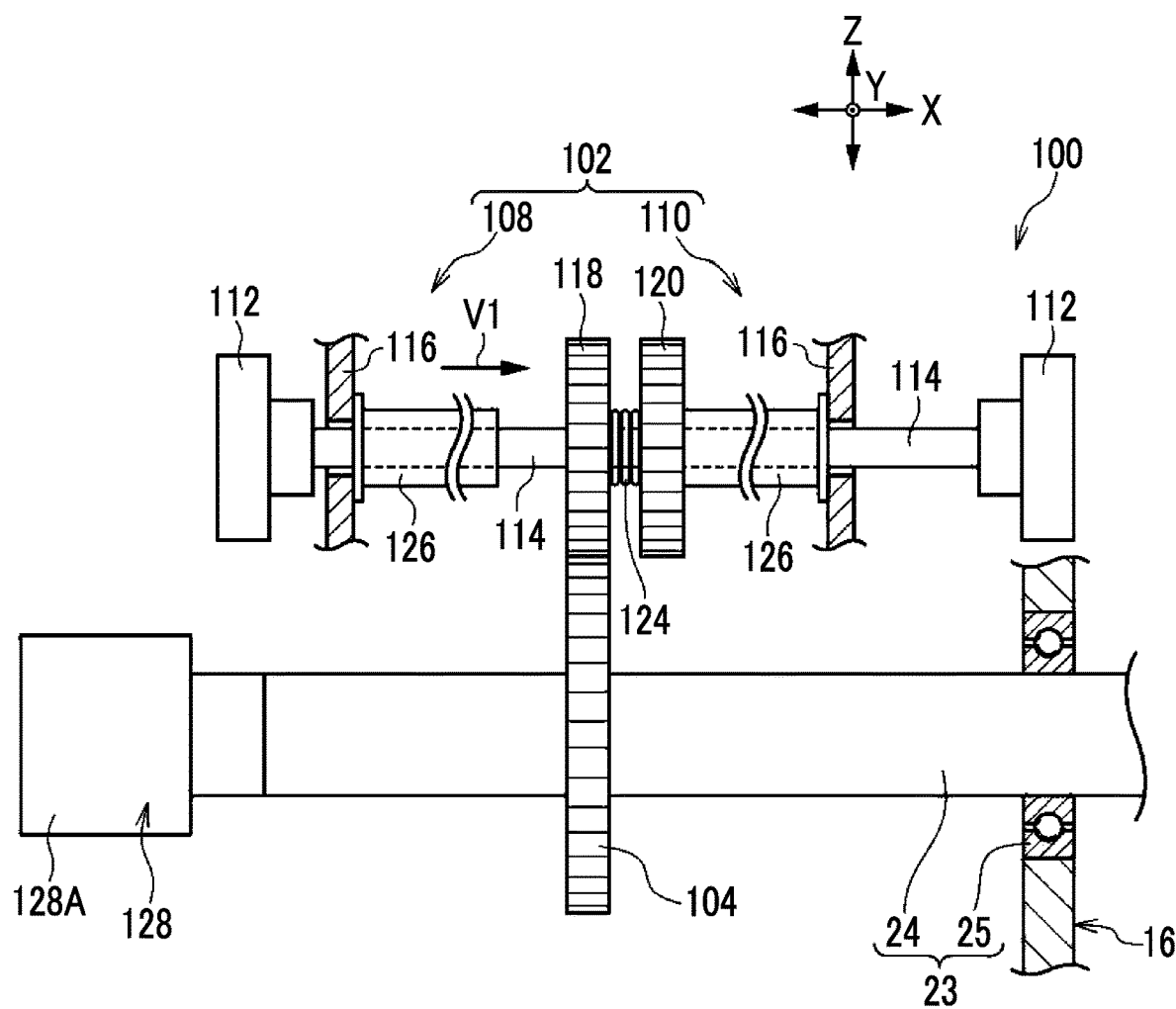
FIG. 11A is an operation view illustrating a state in which one of the operation handles illustrated in FIG. 10 is slid in the axial direction.
Figure 11B:
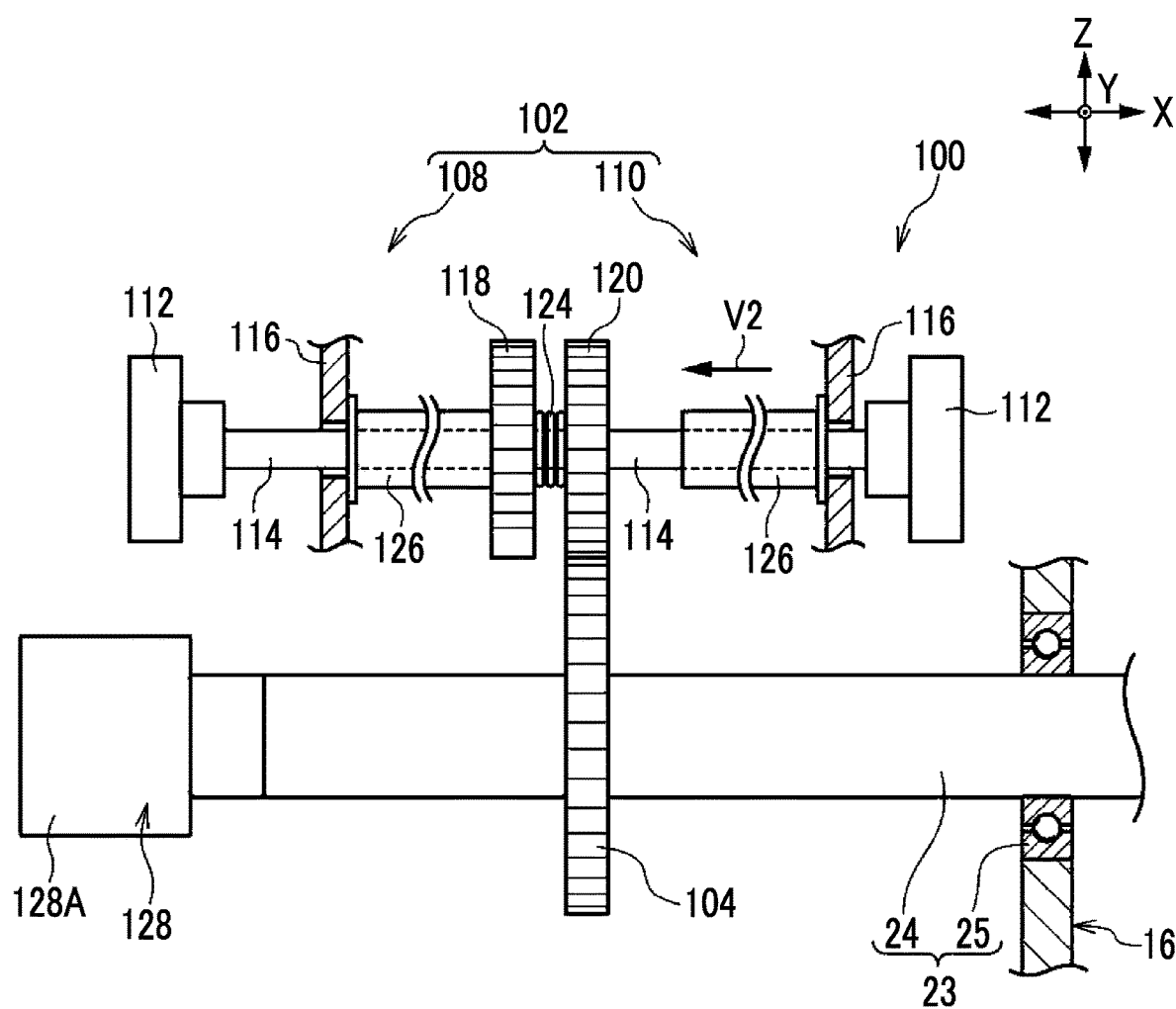
FIG. 11B is an operation diagram illustrating a state in which the other of the operation handles illustrated in FIG. 10 is slid in the axial direction.

As illustrated in FIGS. 11A and 11B, one end of each of the handle shafts 114 of the first operation handle 108 and the second operation handle 110 in the axial direction is exposed from a side wall 116 of the main body 16 to the outside of the connection portion 14 (see FIG. 9). That is, the grip portions 112 provided at the one end of each of the handle shafts 114 in the axial direction protrude from both side surfaces of the main body 16. Therefore, the operator can grip the grip portions 112 from both sides of the main body 16 and operate the first and second operation handles 108 and 110.

The switching mechanism 106 for switching between a valid state in which the input of an operation force from the operation handle 102 to the second rotation mechanism 23 is validated and an invalid state in which the input is invalidated is provided at the other end of the handle shaft 114 located inside the main body 16 in the axial direction.

The switching mechanism 106 has the same configuration as the switching mechanism 66 according to the first embodiment and includes a first gear 118, a second gear 120, and a shaft 122 and a biasing member 124 that are provided between the first gear 118 and the second gear 120 as illustrated in FIG. 10. The first gear 118 is fixed to the other end of the handle shaft 114 of the first operation handle 108 in the axial direction so as to be coaxially rotatable. The second gear 120 is fixed to the other end of the handle shaft 114 of the second operation handle 110 in the axial direction so as to be coaxially rotatable.

A main gear 104 that is fixed to the support shaft 24 is located between the first gear 118 and the second gear 120 in the axial direction of the handle shaft 114. In a case in which the first gear 118 and the second gear 120 are moved to the other end of the handle shaft 114 in the axial direction, the main gear 104 is engaged with the first gear 118 or the second gear 120.

In a case in which the first operation handle 108 is operated, the grip portion 112 of the first operation handle 108 is pushed to slide the first operation handle 108 in the axial direction. Then, as illustrated in FIG. 11A, the handle shaft 114 and the first gear 118 fixed to the other end of the handle shaft 114 in the axial direction are moved to the other end in the axial direction (the direction of an arrow V1 in FIG. 11A).

In this case, the movement of the second gear 120 of the second operation handle 110 to one end of the handle shaft 114 in the axial direction is regulated by a spacer 126 provided between the second gear 120 and the side wall 116. Therefore, the second gear 120 is not moved in the axial direction of the handle shaft 114 and the first gear 118 approaches the second gear 120 against the biasing force of the biasing member 124.

Then, the main gear 104 disposed between the first gear 118 and the second gear 120 is engaged with the first gear 118. In a case in which the main gear 104 and the first gear 118 are engaged with each other, the support shaft 24 and the handle shaft 114 are connected and the first operation handle 108 is switched to the valid state in which the input of the operation force to the second rotation mechanism 23 is valid.

In a case in which the grip portion 112 is rotated with the main gear 104 engaged with the first gear 118, the handle shaft 114 and the first gear 118 are rotated with the rotation of the grip portion 112 and the main gear 104 engaged with the first gear 118 is rotated. Then, as the main gear 104 is rotated, the support shaft 24 is rotated, and the arm 12 (see FIG. 9) to which one end of the support shaft 24 is fixed is rotated about the axis. That is, the first operation handle 108 can be operated to rotate the arm 12.

In a case in which the second operation handle 110 is operated, the grip portion 112 of the second operation handle 110 is pushed to slide the second operation handle 110 in the axial direction as in the case of the first operation handle 108. Then, as illustrated in FIG. 11B, the handle shaft 114 and the second gear 120 fixed to the other end of the handle shaft 114 in the axial direction are moved to the other end in the axial direction (the direction of an arrow V2 in FIG. 11B).

In this case, since the movement of the first gear 118 of the first operation handle 108 to one end of the handle shaft 114 in the axial direction is regulated by the spacer 126 provided between the first gear 118 and the side wall 116. Therefore, the first gear 118 is not moved in the axial direction of the handle shaft 114 and the second gear 120 approaches the first gear 118 against the biasing force of the biasing member 124.

Therefore, the main gear 104 disposed between the first gear 118 and the second gear 120 is engaged with the second gear 120. In a case in which the main gear 104 and the second gear 120 are engaged with each other, the support shaft 24 and the handle shaft 114 are connected and the second operation handle 110 is switched to the valid state in which the input of the operation force to the second rotation mechanism 23 is valid.

In a case in which the grip portion 112 is rotated with the main gear 104 engaged with the second gear 120, the handle shaft 114 and the second gear 120 are rotated with the rotation of the grip portion 112 and the main gear 104 engaged with the second gear 120 is rotated. Then, as the main gear 104 is rotated, the support shaft 24 is rotated, and the arm 12 (see FIG. 9) to which one end of the support shaft 24 is fixed is rotated about the axis. That is, the second operation handle 110 can be operated to rotate the arm 12.

The first operation handle 108 and the second operation handle 110 are biased to one end in the axial direction by the biasing member 124. Therefore, in a case in which the first operation handle 108 and the second operation handle 110 are not operated, that is, in a case in which the grip portion 112 is not pushed, the first gear 118 and the second gear 120 are not engaged with the main gear 104 as illustrated in FIG. 10. As a result, the first operation handle 108 and the second operation handle 110 are switched to the invalid state in which the input of the operation force to the second rotation mechanism 23 is invalid.

An electromagnetic brake 128 is connected to the other end of the support shaft 24. The electromagnetic brake 128 has the same configuration as the electromagnetic brake 78 according to the first embodiment. That is, the electromagnetic brake 128 comprises a housing 128A that is fixed to the main body 16 so as not to be rotatable. The support shaft 24 is rotatably attached to the housing 128A through a rotor that is provided in the housing 128A.

In a case in which the electromagnetic brake 128 is de-energized, a movable iron piece (not illustrated) presses the rotor against the inner wall surface of the housing 128A so as to come into close contact therewith. Therefore, the rotation of the rotor with respect to the housing 128A is locked. Then, the rotation of the rotor with respect to the housing 128A is locked to lock the rotation of the support shaft 24 fixed to the rotor. The rotation of the support shaft 24 is locked to lock the axial rotation of the arm 12 illustrated in FIG. 9 with respect to the bearing 25.

On the other hand, in a case in which the electromagnetic brake 128 is energized, a magnetic force is generated in an electromagnet (not illustrated) that is provided in the housing 128A and the movable iron piece (not illustrated) is attracted to the electromagnet. Therefore, the pressing of the rotor against the inner wall surface of the housing 128A by the movable iron piece is released and the rotor can be rotated with respect to the housing 128A. That is, the rotation of the rotor is unlocked and the rotation of the support shaft 24 is also unlocked by the unlocking of the rotation of the rotor. Therefore, the axial rotation of the arm 12 illustrated in FIG. 9 with respect to the bearing 25 is unlocked.

Operation and Effect

According to the radiography apparatus 100 of this embodiment, the operation handle 102 (the first operation handle 108 and the second operation handle 110) is connected to the second rotation mechanism 23 that rotates the arm 12 with respect to the main body 16. Therefore, the operation handle 102 can input an operation force for rotating the arm 12 to the second rotation mechanism 23 and it is possible to rotate the arm 12 about the axis, without directly operating the arm 12.

Further, according to this embodiment, the operation handle 102 is connected to the second rotation mechanism 23 through the switching mechanism 106. Therefore, the switching mechanism 106 can switch the operative association between the second rotation mechanism 23 and the operation handle 102 and it is possible to prevent the operation handle 102 from being rotated with the rotation of the arm 12 in a case in which the arm 12 is directly rotated.

Further, according to this embodiment, the operation handle 102 can be switched between the valid state and the invalid state by sliding in the axial direction, and the biasing member 124 biases the operation handle 102 in the direction in which the operation handle 102 is switched to the invalid state.

Therefore, the operative association between the second rotation mechanism 23 and the operation handle 102 can be switched by a simple operation. Further, the operation handle 102 can be manually slid in the axial direction against the biasing force of the biasing member 124 to be switched to the valid state. The operation handle 102 can be switched to the invalid state only by releasing the hand from the operation handle 102.

Further, according to this embodiment, in addition to the operation handle 102, the electromagnetic brake 128 is connected to the second rotation mechanism 23. As such, since the electromagnetic brake 128 is connected to the second rotation mechanism 23, it is possible to lock the rotation of the arm 12 as necessary and to suppress the inadvertent rotation of the arm 12.

Other Embodiments

Examples of the embodiments of the present disclosure have been described above. However, the present disclosure is not limited to the above-described embodiments and various modifications and changes can be made without departing from the scope and spirit of the present disclosure. Further, the configurations of each of the above-described embodiments can be appropriately combined with each other.

For example, in the first embodiment, the operation handle 44 is connected to the first rotation mechanism 21 that orbitally rotates the arm 12. In the second embodiment, the operation handle 102 is connected to the second rotation mechanism 23 that rotates the arm 12 about the axis. However, the operation handle may be connected to both the first rotation mechanism 21 and the second rotation mechanism 23.

Further, in the above-described embodiments, the electromagnetic brake 78 or 128 is connected to the first rotation mechanism 21 or the second rotation mechanism 23. However, the electromagnetic brakes 78 and 128 may not be provided and only the operation handle 44 or 102 may be connected to the first rotation mechanism 21 or the second rotation mechanism 23.

In the above-described embodiments, the displacement mechanism for displacing the arm 12 is the rotation mechanism (the first rotation mechanism 21 and the second rotation mechanism 23) that rotates the arm 12. However, the displacement mechanism for displacing the arm 12 is not limited to the rotation mechanism and may be, for example, a slide mechanism 130 that slides the arm 12 as in a modification example illustrated in FIGS. 12 to 14.

Figure 12:
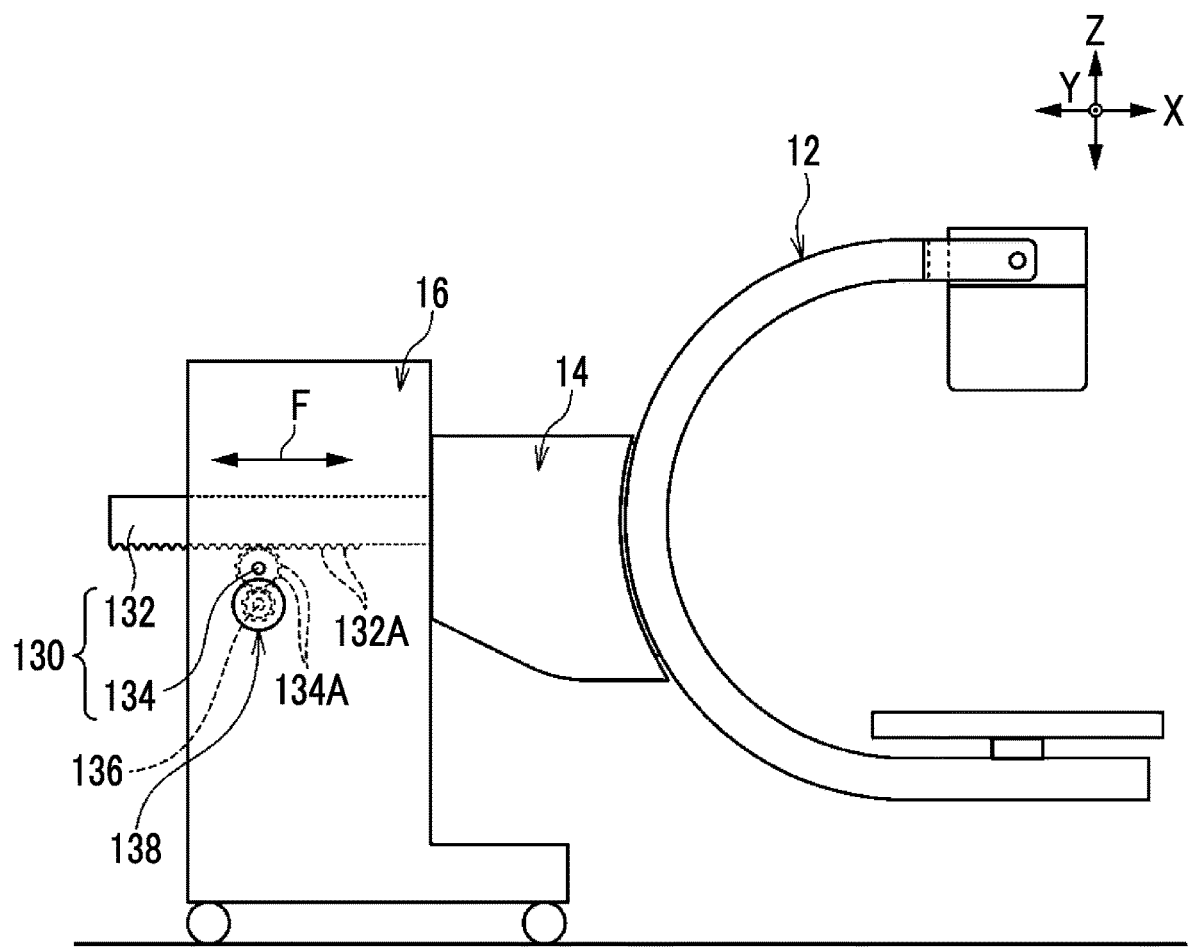
FIG. 12 is an overall side view illustrating an operation handle of a radiography apparatus according to a modification example.

Specifically, as illustrated in FIG. 12, the slide mechanism 130 comprises a rack 132 that has one end fixed to the arm 12 and a pinion 134 that is provided in the main body 16. The rack 132 has a plurality of teeth 132A formed on the lower surface and is attached to the main body 16 so as to be movable in the horizontal direction (X direction). The pinion 134 is a circular gear that has a plurality of teeth 134A formed on the outer peripheral surface and is fixed to the main body 16 so as to be rotatable about the axis.

The teeth 134A of the pinion 134 are engaged with the teeth 132A of the rack 132 such that the rack 132 and the pinion 134 are operatively associated with each other. Therefore, in a case in which the arm 12 is manually slid with respect to the main body 16, the rack slides in the direction of an arrow F and the pinion 134 engaged with the rack 132 is rotated.

Figure 13:
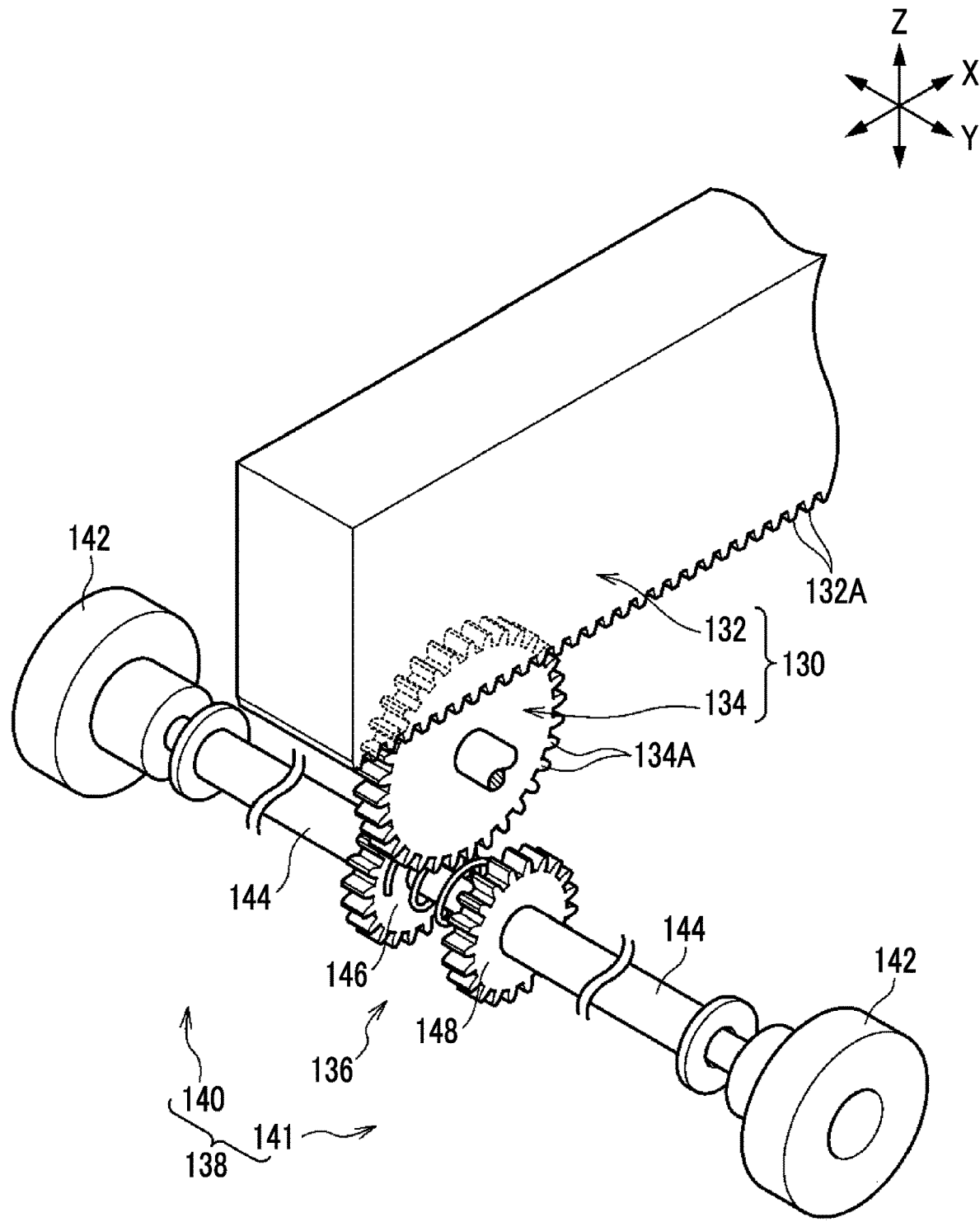
FIG. 13 is a perspective view illustrating the operation handles illustrated in FIG. 12.

Further, an operation handle 138 is connected to the pinion 134 through a switching mechanism 136. The switching mechanism 136 and the operation handle 138 have the same configurations as those in the first and second embodiments. As illustrated in FIG. 13, the operation handle 138 includes a first operation handle 140 and a second operation handle 141.

Figure 14A:
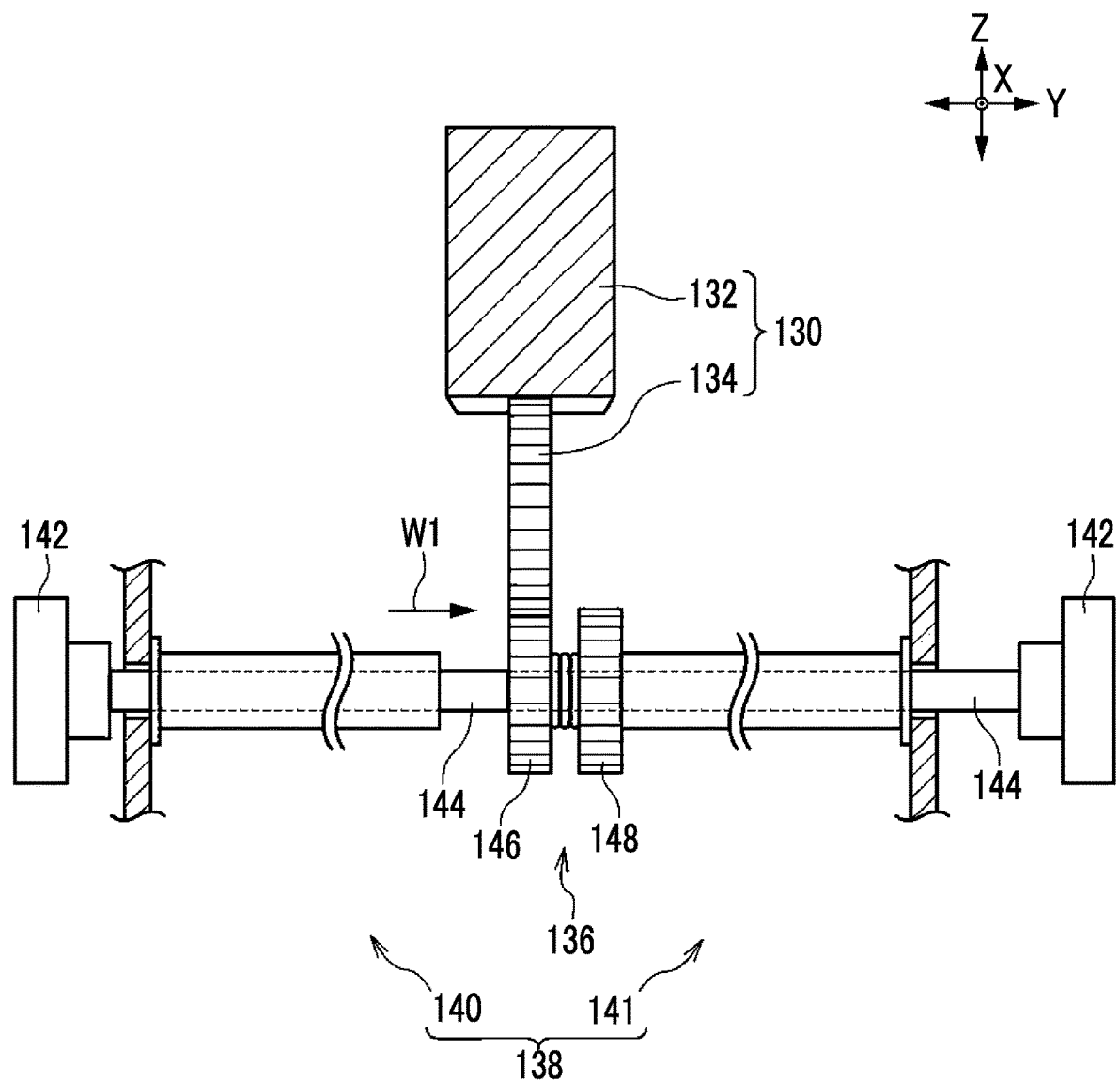
FIG. 14A is an operation diagram illustrating a state in which one of the operation handles illustrated in FIG. 13 is slid in the axial direction.

In a case in which the first operation handle 140 is operated, a grip portion 142 is pushed to slide the first operation handle 140 in the axial direction. Then, as illustrated in FIG. 14A, a handle shaft 144 and a first gear 146 that is fixed to the other end of the handle shaft 144 in the axial direction are moved to the other end in the axial direction (the direction of an arrow W1 in FIG. 14A).

Then, the first gear 146 and the pinion 134 are engaged with each other. In a case in which the first gear 146 and the pinion 134 are engaged with each other, the first operation handle 140 is switched to the valid state in which the input of the operation force to the slide mechanism 130 is valid.

Figure 14B:
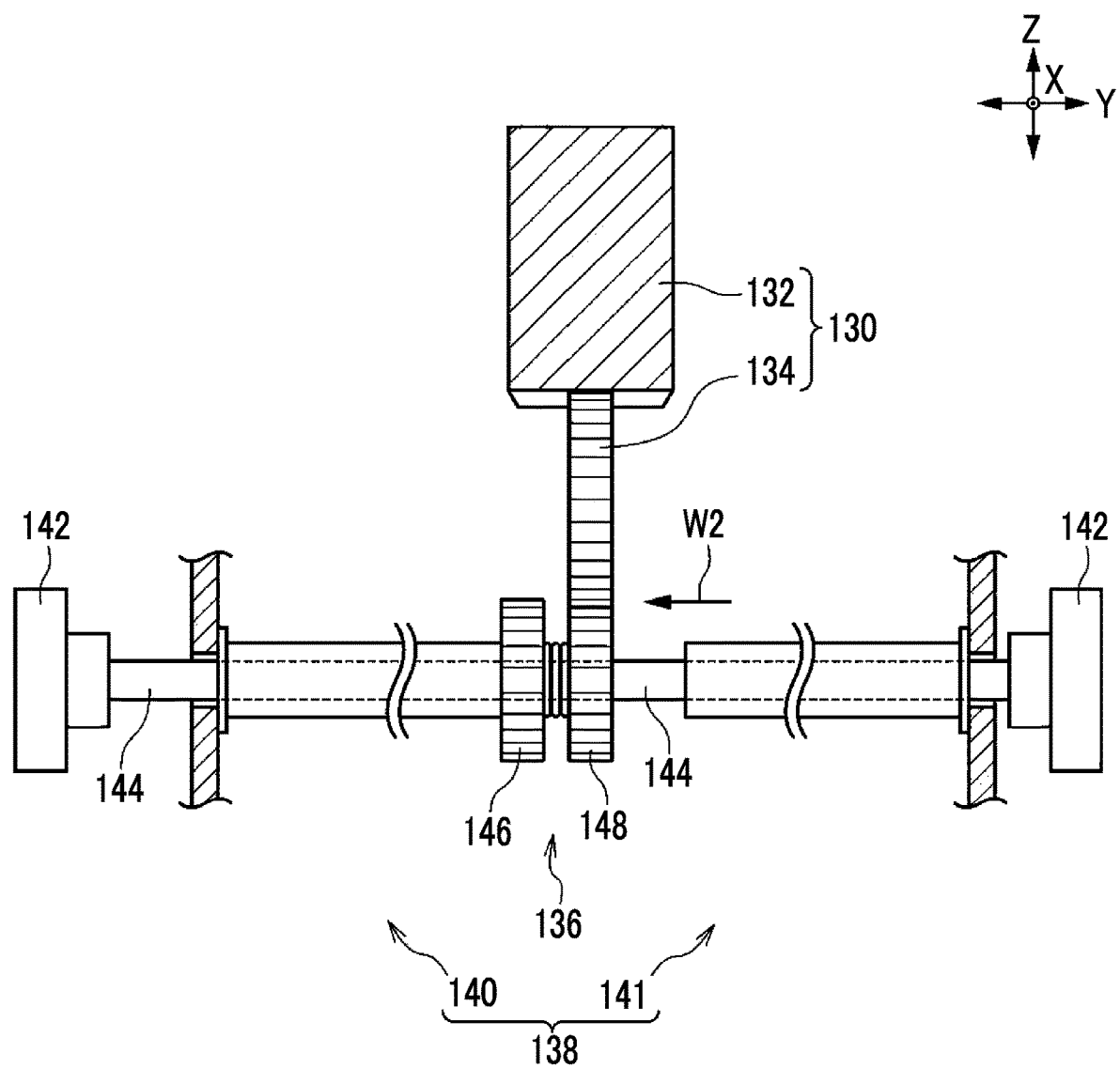
FIG. 14B is an operation diagram illustrating a state in which the other of the operation handles illustrated in FIG. 13 is slid in the axial direction.

In a case in which the second operation handle 141 is operated, the grip portion 142 is pushed to slide the second operation handle 141 in the axial direction. Then, as illustrated in FIG. 14B, the handle shaft 144 and a second gear 148 that is fixed to the other end of the handle shaft 144 in the axial direction are moved to the other end in the axial direction (the direction of an arrow W2 in FIG. 14B).

Then, the second gear 148 and the pinion 134 are engaged with each other. In a case in which the second gear 148 and the pinion 134 are engaged with each other, the second operation handle 141 is switched to the valid state in which the input of the operation force to the slide mechanism 130 is valid.

In a case in which the first operation handle 140 and the second operation handle 141 are not operated, that is, in a case in which the grip portion 142 is not pushed, the first gear 146 and the second gear 148 are engaged with the pinion 134 as illustrated in FIG. 13. Therefore, the first operation handle 140 and the second operation handle 141 are switched to the invalid state in which the input of the operation force to the slide mechanism 130 is invalid.

Figure 15:
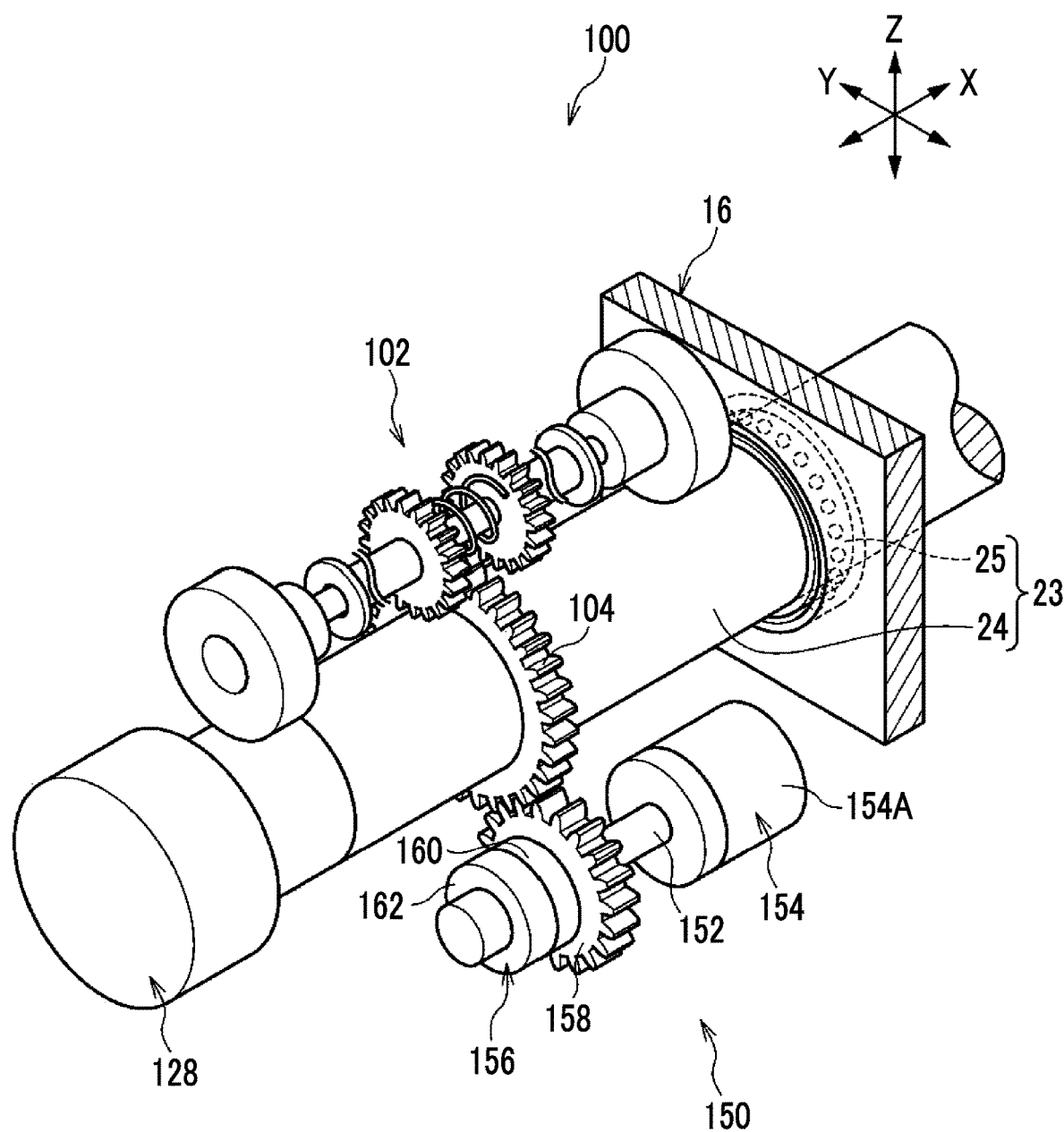
FIG. 15 is a perspective view illustrating a friction mechanism of a radiography apparatus according to a modification example.

As in a modification example illustrated in FIG. 15, in addition to the operation handle 102 and the electromagnetic brake 128, a friction mechanism 150 may be provided in the main body 16 of the radiography apparatus 100 according to the second embodiment. The friction mechanism 150 applies a frictional force to the arm 12 in a direction opposite to the direction in which the arm 12 (see FIG. 9) is rotated.

Specifically, the friction mechanism 150 comprises a friction shaft 152, a frictional force generation unit 154 that is attached to the friction shaft 152 and generates a frictional force, and a clutch 156 that switches connection and disconnection between the support shaft 24 and the friction shaft 152. In addition, a third gear 158 is engaged with the main gear 104 fixed to the support shaft 24.

The friction shaft 152 is supported by the main body 16 through a bearing (not illustrated). Further, the frictional force generation unit 154 is attached to one end of the friction shaft 152 in the axial direction. The frictional force generation unit 154 is, for example, a rotary damper.

That is, the frictional force generation unit 154 comprises a rotor (not illustrated) that is fixed to one end of the friction shaft 152 in the axial direction, a housing 154A that accommodates the rotor, and a viscous body (not illustrated) that consists of oil filled between the rotor and the housing 154A.

In a case in which the friction shaft 152 is rotated, the rotor fixed to the friction shaft 152 is rotated in the housing 154A. In this case, a frictional force acts on the outer peripheral surface of the rotor in a direction opposite to the rotation direction due to the viscous resistance of the viscous body filled in the housing 154A. That is, the frictional force acts on the friction shaft 152 in the direction opposite to the rotation direction.

The clutch 156 is attached to the other end of the friction shaft 152 in the axial direction. The clutch 156 is, for example, an electromagnetic clutch and comprises a housing 160 having an electromagnet (not illustrated) provided therein and a shaft fixing portion 162 that is fixed to the friction shaft 152. The housing 160 and the shaft fixing portion 162 are separated from each other. Further, a biasing member (not illustrated) that biases the housing 160 and the shaft fixing portion 162 in a direction in which they become further away from each other is provided between the housing 160 and the shaft fixing portion 162.

The housing 160 of the clutch 156 is fixed to the third gear 158. The housing 160 and the third gear 158 are not connected to the friction shaft 152. The clutch 156 switches connection and disconnection between the third gear 158 and the friction shaft 152 to switch connection and disconnection between the support shaft 24 and the friction shaft 152.

Specifically, in a case in which the clutch 156 is energized, a magnetic force is generated in the electromagnet provided in the housing 160 and the shaft fixing portion 162 is attracted to the electromagnet against the biasing force of the biasing member (not illustrated). Therefore, the housing 160 and the shaft fixing portion 162 are closely connected.

In a case in which the support shaft 24 is rotated with the housing 160 connected to the shaft fixing portion 162, the frictional force that acts on the friction shaft 152 in a direction opposite to the rotation direction acts on the support shaft 24 through the third gear 158 and the main gear 104. Then, in a case in which the arm 12 illustrated in FIG. 9 is rotated about the axis, the frictional force acts on the arm 12 in a direction opposite to the rotation direction of the arm 12.

In contrast, in a case in which the clutch 156 is de-energized, the housing 160 fixed to the third gear 158 and the shaft fixing portion 162 fixed to the friction shaft 152 are biased by a biasing member (not illustrated) and are separated from each other. Therefore, the housing 160 and the shaft fixing portion 162 are disconnected and the third gear 158 and the friction shaft 152 are disconnected.

Therefore, even in a case in which the support shaft 24 is rotated with the housing 160 disconnected from the shaft fixing portion 162, the frictional force that acts on the friction shaft 152 does not act on the support shaft 24. Therefore, the frictional force that acts on the arm 12 in a case in which the arm 12 is rotated about the axis is less than that in a case in which the clutch 156 is energized.

As described above, in addition to the operation handle 102, the friction mechanism 150 is connected to the second rotation mechanism 23, which makes it possible to change a load due to a manual operation force in a case in which the arm 12 is operated as necessary.

Further, in the above-described embodiments, the arm 12 can be displaced (rotated) by only a manual operation. However, the arm 12 may be rotated by an electric operation, or the manual operation and the electric operation may be switched.

In the above-described embodiments, the first rotation mechanism 21 is configured by the track portion 22B and the pulley shaft 48 provided in the connection portion 14 and the fitting portion 22A formed in the arm 12. However, the first rotation mechanism 21 may have any configuration as long as it can orbitally rotate the arm 12 with respect to the connection portion 14 as a support portion.

For example, the first rotation mechanism may be configured by a pinion (not illustrated) that is fixed to the rotation shaft provided in the connection portion 14 so as to be coaxially rotatable and a rack (not illustrated) which is provided on the outer peripheral surface of the arm 12 and in which a plurality of teeth engaged with the pinion are formed.

Further, in the above-described embodiments, the operation handle 44 or 102 is connected to the first rotation mechanism 21 or the second rotation mechanism 23 through the switching mechanism 66 or 106. However, the switching mechanism 66 or 106 may not be provided and the operation handle 44 or 102 may be directly connected to the first rotation mechanism 21 or the second rotation mechanism 23. In this configuration, in a case in which the arm 12 is directly rotated, the operation handle 44 or 102 is rotated with the rotation of the arm 12. It is possible to simplify the configuration of a connection mechanism between the operation handle 44 or 102 and the first rotation mechanism 21 or the second rotation mechanism 23.

Further, in the above-described embodiments, the switching mechanism 66 or 106 comprises the biasing member 74 or 124 that biases the first gear 68 or 118 and the second gear 70 or 120 in the direction in which they become further away from each other. However, the biasing member 74 or 124 may not be provided. In this case, the grip portion 60 or 112 can be manually slid to the other end of the handle shaft 62 or 114 in the axial direction to switch the operation handle 44 or 102 to the valid state. The grip portion 60 or 112 can be manually slid to one end of the handle shaft 62 or 114 in the axial direction to switch the operation handle 44 or 102 to the invalid state.

Further, in the above-described embodiments, the operation handle 44 or 102 includes the first operation handle 56 or 108 and the second operation handle 58 or 110. However, the number of operation handles is not limited to two. For example, at least one operation handle may be provided in the connection portion 14 or the main body 16.

Further, in each of the above-described embodiments, the arm (C-arm) that can be orbitally rotated and can be rotated about the axis has been described as an example of the arm 12. However, an arm (for example, a U-arm having a U-shape in a side view) that can be only rotated about the axis may be used. Similarly to the C-arm, the U-arm can hold, for example, the irradiation unit 18 and the image receiving unit 20 in a posture in which they face each other.

In addition, X-rays have been described as an example of the radiation. However, the present disclosure is not limited to the X-rays. For example, y-rays may be used.

In each of the above-described embodiments, for example, the following various processors can be used as a hardware structure of processing units performing various processes, such as the control unit 28. The various processors include, for example, a CPU which is a general-purpose processor executing software to function as various processing units as described above, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:
1. A radiography apparatus comprising:
   an irradiation unit that emits radiation;
   an arm that is capable of holding the irradiation unit and an image receiving unit that receives the radiation, which has been emitted from the irradiation unit and transmitted through a subject, in a facing posture;
   a support portion that supports the arm;
   a displacement mechanism that displaces the arm with respect to the support portion; and
   an operation handle that is provided independently of the arm and is manually operated to input an operation force for displacing the arm with respect to the displacement mechanism.
2. The radiography apparatus according to claim 1, wherein the arm is capable of being displaced by only a manual operation.

3. The radiography apparatus according to claim 1,
wherein the displacement mechanism is a rotation mechanism that rotates the arm.

4. The radiography apparatus according to claim 3,
wherein the rotation mechanism has a rotation shaft that is rotated with the rotation of the arm,
the operation handle has a handle shaft that is rotated with rotation of the operation handle, and
the operation force is input to the rotation mechanism by a connection between the rotation shaft and the handle shaft.

5. The radiography apparatus according to claim 4, further comprising:
a switching mechanism that switches between a valid state in which the input of the operation force from the operation handle to the rotation mechanism is validated and an invalid state in which the input is invalidated.

6. The radiography apparatus according to claim 5,
wherein the switching mechanism slides the operation handle in an axial direction to switch between the valid state and the invalid state.

7. The radiography apparatus according to claim 5,
wherein the switching mechanism biases the operation handle in a direction in which the operation handle is switched to the invalid state.

8. The radiography apparatus according to claim 4,
wherein the arm has an arc shape in a side view,
the rotation mechanism includes a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft, and
the arm is moved with respect to the track portion to be orbitally rotatable about a center of the arc shape as a rotation center.

9. The radiography apparatus according to claim 4,
wherein the rotation mechanism includes a second rotation mechanism comprising a second rotation shaft as the rotation shaft that has one end fixed to the arm and a bearing that is provided in the support portion, and
the arm is rotated about the second rotation shaft with respect to the bearing to reverse positions of the irradiation unit and the image receiving unit with respect to the subject.

10. The radiography apparatus according to claim 2,
wherein the displacement mechanism is a rotation mechanism that rotates the arm.

11. The radiography apparatus according to claim 6,
wherein the switching mechanism biases the operation handle in a direction in which the operation handle is switched to the invalid state.

12. The radiography apparatus according to claim 5,
wherein the arm has an arc shape in a side view,
the rotation mechanism includes a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft, and
the arm is moved with respect to the track portion to be orbitally rotatable about a center of the arc shape as a rotation center.

13. The radiography apparatus according to claim 6,
wherein the arm has an arc shape in a side view,
the rotation mechanism includes a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft, and
the arm is moved with respect to the track portion to be orbitally rotatable about a center of the arc shape as a rotation center.

14. The radiography apparatus according to claim 7,
wherein the arm has an arc shape in a side view,
the rotation mechanism includes a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft, and
the arm is moved with respect to the track portion to be orbitally rotatable about a center of the arc shape as a rotation center.

15. The radiography apparatus according to claim 11,
wherein the arm has an arc shape in a side view,
the rotation mechanism includes a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft, and
the arm is moved with respect to the track portion to be orbitally rotatable about a center of the arc shape as a rotation center.

16. The radiography apparatus according to claim 5,
wherein the rotation mechanism includes a second rotation mechanism comprising a second rotation shaft as the rotation shaft that has one end fixed to the arm and a bearing that is provided in the support portion, and
the arm is rotated about the second rotation shaft with respect to the bearing to reverse positions of the irradiation unit and the image receiving unit with respect to the subject.

17. The radiography apparatus according to claim 6,
wherein the rotation mechanism includes a second rotation mechanism comprising a second rotation shaft as the rotation shaft that has one end fixed to the arm and a bearing that is provided in the support portion, and
the arm is rotated about the second rotation shaft with respect to the bearing to reverse positions of the irradiation unit and the image receiving unit with respect to the subject.

18. The radiography apparatus according to claim 7,
wherein the rotation mechanism includes a second rotation mechanism comprising a second rotation shaft as the rotation shaft that has one end fixed to the arm and a bearing that is provided in the support portion, and
the arm is rotated about the second rotation shaft with respect to the bearing to reverse positions of the irradiation unit and the image receiving unit with respect to the subject.

19. The radiography apparatus according to claim 11,
wherein the rotation mechanism includes a second rotation mechanism comprising a second rotation shaft as the rotation shaft that has one end fixed to the arm and a bearing that is provided in the support portion, and the arm is rotated about the second rotation shaft with respect to the bearing to reverse positions of the irradiation unit and the image receiving unit with respect to the subject.

20. The radiography apparatus according to claim 8, wherein the rotation mechanism includes a second rotation mechanism comprising a second rotation shaft as the rotation shaft that has one end fixed to the arm and a bearing that is provided in the support portion, and the arm is rotated about the second rotation shaft with respect to the bearing to reverse positions of the irradiation unit and the image receiving unit with respect to the subject.

* * * * *